US011609231B2

(12) United States Patent
Klatt et al.

(10) Patent No.: US 11,609,231 B2
(45) Date of Patent: Mar. 21, 2023

(54) DETECTION OF AUTOANTIBODIES FOR DIAGNOSING DEGENERATIVE DISEASES OF THE SKELETAL SYSTEM

(71) Applicant: UNIVERSITÄT ZU KÖLN, Cologne (DE)

(72) Inventors: Andreas R. Klatt, Cologne (DE); Johannes Ruthard, Hürth (DE); Benedikt Ostendorf, Neuss (DE); Matthias Schneider, Düsseldorf (DE); Georg Pongratz, Pettendorf/Kneiting (DE); Gabriele Hermes, Cologne (DE)

(73) Assignee: UNIVERSITÄT ZU KÖLN, Cologne (DE)

( * ) Notice: Subject to any disclaimer, the term of this patent is extended or adjusted under 35 U.S.C. 154(b) by 304 days.

(21) Appl. No.: 16/954,935

(22) PCT Filed: Dec. 12, 2018

(86) PCT No.: PCT/EP2018/084451
§ 371 (c)(1),
(2) Date: Jun. 17, 2020

(87) PCT Pub. No.: WO2019/121187
PCT Pub. Date: Jun. 27, 2019

(65) Prior Publication Data
US 2021/0109097 A1     Apr. 15, 2021

(30) Foreign Application Priority Data

Dec. 21, 2017  (EP) .................................... 17209795

(51) Int. Cl.
*G01N 33/53*    (2006.01)
*G01N 33/564*   (2006.01)

(52) U.S. Cl.
CPC ... *G01N 33/564* (2013.01); *G01N 2333/4727* (2013.01); *G01N 2333/78* (2013.01); *G01N 2800/102* (2013.01); *G01N 2800/50* (2013.01); *G01N 2800/56* (2013.01)

(58) Field of Classification Search
None
See application file for complete search history.

(56) References Cited

U.S. PATENT DOCUMENTS 5,736,343 A * 4/1998 Landry ................. G01N 33/68
435/7.6
2012/0135427 A1* 5/2012 Kypros ................. G01N 33/74
435/7.92

FOREIGN PATENT DOCUMENTS

| JP | 2004117160 A | 4/2004 |
| JP | 2004279334 A | 10/2004 |
| WO | 2014016584 A2 | 1/2014 |

OTHER PUBLICATIONS

Torzewski et al., Animal Models of C-Reactive Protein, Hindawl Publishing Corporation, Mediators of Inflammation, vol. 2014, pp. 1-7. (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Hinton et al., Osteoarthritis: Diagnosis and Therapeutic considerations, Practical Therapeutics, Mar. 1, 2002, vol. 65, No. 5, pp. 841-848. (Year: 2002).*
Kuhne et al., Persistent high serum levels of cartilage oligomeric matrix protein in a subgroup of patients with traumatic knee injury, Rheumatol Int, 1998, pp. 21-25. (Year: 1998).*
Csoka et al., The incidence and specificity of antibodies to different types of collagen (II, minor collagens, IX) in arthrosis, Fresenius Z Anal Chem, 1986, Posters A, 324:248. (Year: 1986).*
Clague et al., Absence of autoimmunity to type II collagen in gneeralised nodal osteoarthritis, Annals of the Rheumatic Diseases 1991, 50, pp. 769-771. (Year: 1991).*
Henjes et al., "Analysis of Autoantibody Profiles in Osteoarthritis Using Comprehensive Protein Array Concepts," Journal of Proteome Research, Nov. 7, 2014, vol. 13, Iss. 11, pp. 5218-5229.
Jeschke et al., "Deficiency of Thrombospondin-4 in Mice Does Not Affect Skeletal Growth or Bone Mass Acquisition, but Causes a Transient Reduction of Articular Cartilage Thickness," PLoS One, Dec. 2, 2015, vol. 10, No. 12, p. e0144272.
Paróczai et al., "Estimation of Serum Anticollagen and the Antibodies Against Chondrocyte Membrane Fraction: Their Clinical Diagnostic Significance in Osteoarthritis," Clinical Biochemistry, Apr. 1, 1988, vol. 21, Iss. 2, pp. 117-121.
International Search Report and Written Opinion issued in corresponding International Patent Application No. PCT/EP2018/084451, dated Apr. 3, 2019 (23 pages).
Acharya et al., "Cartilage oligomeric matrix protein and its binding partners in the cartilage extracellular matrix nteraction, regulation and role in chondrogenesis," Matrix Biology, 2014, vol. 37, pp. 102-111 (10 pages).
Aletaha et al., "2010 Rheumatoid Arthritis Classification Criteria," Arthritis & Rheumatism, Sep. 2010, vol. 62, No. 9, pp. 2569-2581 (13 pages).

(Continued)

*Primary Examiner* — Gary Counts
(74) *Attorney, Agent, or Firm* — Melissa Hunter-Ensor; Nicholas R. Ballor; Greenberg Traurig, LLP

(57) ABSTRACT

Methods, kits, and active ingredients for diagnosing or treating arthritis or a degenerative disease of the skeletal system, or for selection of subjects for therapy. The methods for diagnosing arthritis involve the detection of an autoantibody, which is associated with arthritis, or excluding the presence of an autoantibody against collagen II. The methods for diagnosing a degenerative disease of the skeletal system, involve the detection of an autoantibody against thrombospondin-4 or COMP. The kits contain a detection agent for an autoantibody and can be used for diagnosing arthritis or a degenerative disease of the skeletal system. The active ingredient can be used for treating or preventing autoimmune-associated arthritis.

14 Claims, No Drawings
Specification includes a Sequence Listing.

(56) References Cited

OTHER PUBLICATIONS

Altman et al., "Development of Criteria for the Classification and Reporting of Osteoarthritis: Classification of Osteoarthritis of the Knee," Arthritis & Rheumatism, Aug. 1986, vol. 29, No. 8, pp. 1039-1049 (11 pages).

Altman et al., "The American College of Rheumatology Criteria for the Classification and Reporting of Osteoarthritis of the Hand," Arthritis & Rheumatism, Nov. 1990, vol. 33, No. 11, pp. 1601-1610 (10 pages).

Altman, Roy D., "Classification of Disease: Osteoarthritis," Seminars in Arthritis and Rheumatism, Jun. 1991, vol. 20, No. 6, Suppl. 2, pp. 40-47 (8 pages).

Deane, Kevin D., "Preclinical Rheumatoid Arthritis (Autoantibodies): An Updated Review," Current Rheumatology Reports, 2014, vol. 16, Article No. 419, pp. 1-9 (9 pages).

Dicesare et al., "Cartilage Oligomeric Matrix Protein: Isolation and Characterization from Human Articular Cartilage," Journal of Orthopaedic Research, 1995, vol. 13, No. 3, pp. 422-428 (7 pages).

Halasz et al., "COMP Acts as a Catalyst in Collagen Fibrillogenesis," The Journal of Biological Chemistry, Oct. 26, 2007, vol. 282, No. 43, pp. 31166-31173 (9 pages).

Haudenschild et al., "Enhanced Activity of Transforming Growth Factor β1 (TGF-β1) Bound to Cartilage Oligomeric Matrix Protein," The Journal of Biological Chemistry, Dec. 16, 2011, vol. 286, No. 50, pp. 43250-43258 (10 pages).

Ishida et al., "Cartilage oligomeric matrix protein enhances osteogenesis by directly binding and activating bone morphogenetic protein-2," Bone, 2013, vol. 55, pp. 23-35 (13 pages).

Karlin et al., "Methods for assessing the statistical significance of molecular sequence features by using general scoring schemes," Proceedings of the National Academy of Sciences USA, Mar. 1990, vol. 87, pp. 2264-2268 (5 pages).

Karlin et al., "Applications and statistics for multiple high-scoring segments in molecular sequences," Proceedings of the National Academy of Sciences USA, Jun. 1993, vol. 90, pp. 5873-5877 (5 pages).

Karlsson et al., "Genome-wide expression profiling reveals new candidate genes associated with osteoarthritis," Osteoarthritis and Cartilage, 2010, vol. 18, pp. 581-592 (12 pages).

Kleerekoper et al., "Disease-causing Mutations in Cartilage Oligomeric Matrix Protein Cause an Unstructured Ca2+ Binding Domain," The Journal of Biological Chemistry, Mar. 22, 2002, vol. 277, No. 12, pp. 10581-10589 (10 pages).

Kvansakul et al., "Structure of a thrombospondin C-terminal fragment reveals a novel calcium core in the type 3 repeats," The EMBO Journal, 2004, vol. 23, No. 6, pp. 1223-1233 (11 pages).

Lau et al., "The cartilage-specific lectin C-type lectin domain family 3 member A (CLEC3A) enhances tissue plasminogen activator-mediated plasminogen activation," The Journal of Biological Chemistry, 2018, vol. 293, No. 1, pp. 203-214 (13 pages).

Lawler et al., "Characterization of Human Thrombospondin-4," The Journal of Biological Chemistry, Feb. 10, 1995, vol. 270, No. 6, pp. 2809-2814 (7 pages).

Neame et al., "The cartilage-derived C-type lectin (CLECSF1): structure of the gene and chromosomal location," Biochimica et Biophysica Acta, 1999, vol. 1446, pp. 193-202 (10 pages).

Needleman et al., "A General Method Applicable to the Search for Similarities in the Amino Acid Sequence of Two Proteins," Journal of Molecular Biology, 1970, vol. 48, pp. 443-453 (11 pages).

Newton et al., "Characterization of Human and Mouse Cartilage Oligomeric Matrix Protein," Genomics, 1994, vol. 24, pp. 435-439 (5 pages).

Orlandi et al., "Cloning immunoglobulin variable domains for expression by the polymerase chain reaction," Proceedings of the National Academy of Sciences USA, May 1989, vol. 86, pp. 3833-3837 (5 pages).

Pearson et al., "Improved tools for biological sequence comparison," Proceedings of the National Academy of Sciences USA, Apr. 1988, vol. 85, pp. 2444-2448 (5 pages).

Rosenberg et al., "Cartilage Oligomeric Matrix Protein Shows High Affinity Zinc-dependent Interaction with Triple Helical Collagen," The Journal of Biological Chemistry, Aug. 7, 1998, vol. 273, No. 32, pp. 20397-20403 (8 pages).

Smith et al., "Comparison of Biosequences," Advances in Applied Mathematics, 1981, vol. 2, pp. 482-489 (8 pages).

Stoll et al., "Elevated IgG autoantibody production in oligoarticular juvenile idiopathic arthritis may predict a refractory course," Clinical and Experimental Rheumatology, 2011, vol. 29, No. 4, pp. 736-742 (13 pages).

Tsunezumi et al., "Matrilysin (MMP-7) Cleaves C-Type Lectin Domain Family 3 Member A (CLEC3A) on Tumor Cell Surface and Modulates its Cell Adhesion Activity," Journal of Cellular Biochemistry, 2009, vol. 106, pp. 693-702 (10 pages).

Vogel et al., "Specific inhibition of type I and type II collagen fibrillogenesis by the small proteoglycan of tendon," The Biochemical Journal, 1984, vol. 223, pp. 587-597 (11 pages).

Winter et al., "Man-made antibodies," Nature, Jan. 24, 1991, vol. 349, pp. 293-299 (7 pages).

"ACR Diagnostic Guidelines," Johns Hopkins Arthritis Center, pp. 1-32, Sep. 22, 2022 <www.hopkinsarthritis.org/physician-corner/education/arthritis-education-diagnostic-guidelines/>.

"Easy Fisher Exact Test Calculator," Social Science Statistics, p. 1, Aug. 3, 2022 <www.socscistatistics.com/tests/fisher/default2.aspx>.

\* cited by examiner

DETECTION OF AUTOANTIBODIES FOR DIAGNOSING DEGENERATIVE DISEASES OF THE SKELETAL SYSTEM

This application is the U.S. national phase application, pursuant to 35 U.S.C. § 371, of PCT International Application Ser. No.: PCT/EP2018/084451, filed Dec. 12, 2018, designating the United States, which claims priority to European Patent Application No.17209795.8, filed Dec. 21, 2017, the entire contents of which are incorporated herein by reference.

This application contains a Sequence Listing which has been submitted electronically in ASCII format and is hereby incorporated by reference in its entirety. The ASCII copy, created Dec. 30, 2020, is named 194538_010202_US_SL.txt and is 29,725 bytes in size.

Arthrosis is the most common degenerative joint disease worldwide. About two thirds of people over 65 years of age are affected by the disease. The etiology of arthrosis is very largely unknown. The most important arthrosis risk factors include age, overload and genetic predisposition. Currently, disease-modifying, drug-based therapy does not exist and fundamental problems in the development of drugs are the unknown etiology and the complex pathological mechanisms of arthrosis.

A further problem in the development of a disease-modifying drug for arthrosis is the lack of sensitive biochemical markers, by means of which the success of a therapy can be checked. Arthrosis is currently diagnosed through anamnestic data, exclusion of other joint diseases, radiological examinations and arthroscopy. Imaging examinations lead to a strain on the patient and are associated with huge effort and costs, but are only roughly informative about the disease stage and can only describe the later disease stages. Therapy or course monitoring and classification of the disease stage is hardly possible with the methods to date. The identification and validation of a cartilage- or bone-specific molecule as biochemical marker of arthrosis has not been possible to date. Thus, valid biochemical markers for diagnosing arthrosis do not currently exist.

Dean et al. (2014) describe autoantibody measurement in the preclinical stage of rheumatoid arthritis.

Stoll et al. (2011) describe autoantibody production in juvenile idiopathic arthritis as a marker for the disease course. Autoantibodies against a multiplicity of antigens were determined, including also proteins of the extracellular matrix.

Jescke et al. describe thrombospondin-4 as a constituent of joint cartilage. The authors also measured the concentration of thrombospondin-4 in the serum of arthrosis patients. The concentration of thrombospondin-4 is not significantly different compared to healthy control subjects and is therefore not a valid biomarker.

Thus, the determination of autoantibodies for diagnosing rheumatoid arthritis, but not arthrosis, is known in the prior art. Whereas the classic rheumatoid factors are antibodies (usually of the IgM class) which recognize the Fc region of other antibodies, autoantibodies directed against antigens released by proteins in the course of degeneration processes have recently increasingly come to the fore. As described in Stoll et al. (2011), these also include components of the extracellular matrix. The essential features of the present invention, namely the determination of autoantibodies against thrombospondin-4, COMP and/or CLEC3A in arthrosis, are not described in the prior art, however.

Thus, there is a need for methods which allow the determination of arthrosis or of degenerative diseases of the skeletal system in general in a subject. Furthermore, there is a need for methods which allow assessment of the disease stage and allow therapy or course monitoring.

The present invention describes methods which allow the detection of arthrosis in an individual and the assessment of the stage and progression of arthrosis. The inventors mentioned here have discovered that, surprisingly, arthrosis is associated with the formation of autoantibodies against constituents of cartilage or bone and the degradation products thereof. When cartilage or bone degenerates, matrix constituents such as, for example, thrombospondin-4 (TSP-4), COMP and CLEC3A are continuously released. Since the cartilage tissue is presented to the immune system only to a lesser extent, what may occur in the course of the disease is the stimulation and formation of autoantibodies against constituents of cartilage or bone or against neoepitopes which arise in the course of the disease in the proteolytic degradation of said constituents. It is assumed, then, by the inventors that autoantibodies against cartilage matrix proteins, for example TSP-4, COMP and/or CLEC3A, are formed depending on the release amount of said matrix proteins.

Surprisingly, the inventors mentioned here were able to detect anti-TSP-4 autoantibodies in the serum of arthrosis patients. Moreover, autoreactive bands distinctly smaller than full-length TSP-4 were detected in the serum of further arthrosis patients. Degradation products of TSP-4 are presumably concerned here. Surprisingly, the inventors mentioned here were alternatively or additionally able to detect anti-COMP autoantibodies and/or anti-CLEC3A autoantibodies in the blood of arthrosis patients, with a combined detection of anti-TSP-4 autoantibodies and anti-COMP autoantibodies and/or anti-CLEC3A autoantibodies leading to an increased arthrosis detection rate in comparison with individual detection of the autoantibodies. In the case of healthy subjects, it was not possible to detect anti-TSP-4 and anti-CLEC3A autoantibodies, and anti-COMP autoantibodies were detected with very low frequency. Furthermore, the inventors mentioned here found that it was not possible to detect anti-collagen II autoantibodies in any of the subjects for whom arthrosis had been diagnosed with conventional methods, whereas it was possible to detect anti-collagen II autoantibodies in subjects for whom arthrosis had not been diagnosed with conventional methods. These findings are therefore surprising in that no link with the formation of autoantibodies was previously found in the case of arthrosis and that no pathomechanistic significance was attributed to autoantibodies.

The inventors mentioned here were also able to detect anti-TSP-4 autoantibodies or anti-COMP autoantibodies in the serum of patients with rheumatoid arthritis diagnosed by conventional methods, with some patients exhibiting extremely high concentrations compared with other RA patients.

Thus, anti-TSP-4 autoantibodies, anti-COMP autoantibodies or anti-CLEC3A autoantibodies or autoantibodies against other constituents of cartilage or bone and degradation products or fragments thereof, alone or in combination, can serve as biochemical markers of arthrosis. The detection of anti-TSP-4 autoantibodies, anti-COMP autoantibodies or anti-CLEC3A autoantibodies or autoantibodies against other constituents of cartilage or bone or of degradation products thereof, alone or in combination, and autoantibody titer determinations in samples from a subject allow not only the diagnosis of the disease, but also therapy or course monitoring and diagnosis of the stage of arthrosis. Since anti-TSP-4 autoantibodies or anti-COMP autoantibodies have also been detected in sera from RA patients, it is first necessary to exclude RA patients when diagnosing arthrosis with detection of said autoantibodies. Only then can a diagnosis of arthrosis be made according to the method of the present invention. The sensitivity of detection can be additionally increased when the subject is tested for the presence of anti-collagen II autoantibodies. If arthrosis was diagnosed for the subject on the basis of the presence of anti-TSP-4 autoantibodies, anti-COMP autoantibodies and/or anti-CLEC3A autoantibodies or autoantibodies against other constituents of cartilage or bone and degradation products or fragments thereof, alone or in combination, then the absence of the detection of anti-collagen II autoantibodies can be judged to be a further indication that arthrosis is present. Furthermore, the detection of anti-collagen II autoantibodies in a subject can be judged to be an indication that the subject does not have arthrosis or has no risk of developing arthrosis.

In a 1st aspect, the present invention relates to a method for diagnosing arthrosis (including osteochondrosis) or the risk of developing arthrosis in a subject, the subject not having rheumatoid arthritis, comprising the detection of an autoantibody associated with arthrosis in a sample originating from the subject.

In one embodiment thereof, the present invention relates to said method, wherein the method comprises the exclusion of rheumatoid arthritis in the subject.

In one embodiment thereof, the present invention relates to said method, wherein said method furthermore comprises the exclusion of the presence of an autoantibody against collagen II or a degradation product or a fragment thereof, preferably wherein said method comprises the detection of an autoantibody against collagen II or a degradation product or a fragment thereof, more preferably wherein said method comprises the detection of an autoantibody against collagen II or a degradation product or a fragment thereof using a detection agent for detecting an autoantibody against collagen II or a degradation product or a fragment thereof.

In one embodiment thereof, the present invention relates to said method, wherein said method comprises the detection of an autoantibody against thrombospondin-4 (TSP-4) or a degradation product or a fragment thereof or the detection of an autoantibody against COMP or a degradation product or a fragment thereof.

In one embodiment thereof, the present invention relates to said method, wherein the course of arthrosis is monitored, comprising the detection of the autoantibody at various time points; or wherein the stage of arthrosis is diagnosed.

In one embodiment thereof, the present invention relates to said method, wherein said method comprises the detection of at least two autoantibodies, preferably wherein said method comprises the detection of an autoantibody against thrombospondin-4 (TSP-4) or a degradation product or a fragment thereof and the detection of an autoantibody against COMP or a degradation product or a fragment thereof; or preferably wherein said method comprises the detection of an autoantibody against thrombospondin-4 (TSP-4) or a degradation product or a fragment thereof and the detection of an autoantibody against CLEC3A or a degradation product or a fragment thereof; more preferably wherein said method comprises the detection of an autoantibody against thrombospondin-4 (TSP-4) or a degradation product or a fragment thereof, the detection of an autoantibody against COMP or a degradation product or a fragment thereof and the detection of an autoantibody against CLEC3A or a degradation product or a fragment thereof.

In one embodiment thereof, the present invention relates to said method, wherein the autoantibody against a neoepitope of a degradation product of a protein, against which the autoantibody is directed.

In one embodiment thereof, the present invention relates to said method, wherein the detection is carried out using a detection agent, preferably wherein the detection agent is capable of binding to the antigen-binding region of the autoantibody, more preferably wherein the detection agent is TSP-4 or a degradation product or a fragment thereof, COMP or a degradation product or a fragment thereof and/or CLEC3A or a degradation product or a fragment thereof.

In one embodiment thereof, the present invention relates to said method, wherein the sample is body fluid, preferably blood, serum, blood plasma, synovial fluid or urine, muscle or cartilage tissue, synovial membrane or tendon.

The term "comprises", "comprise", "comprising", etc., as used herein, means the inclusion of the features disclosed and further features not specifically mentioned. The term "comprises", "comprise", "comprising", etc., is also understood in the sense of "consisting of" the features disclosed, without inclusion of features other than the ones disclosed. For instance, the method of the present invention can comprise further method steps, but can also only consist of the steps specified. The kit of the present invention can, too, comprise further components, but can also only consist of the components specified.

Thrombospondin-4 is a protein encoded by the TSP-4 gene in humans. The protein belongs to the thrombospondin protein family. Thrombospondin family members are extracellular, adhesive glycosylated matrix proteins expressed in a widespread manner in vertebrates (Lawler et al., 1995). Five thrombospondin proteins, thrombospondin-1 to thrombospondin-4 and cartilage oligomeric matrix protein (COMP), are known. The members of the thrombospondin family are activated during cell reconstruction processes and mediate cell-to-cell and cell-to-matrix interactions. Thrombospondin-4, a pentameric protein, plays a role in cellular migration, adhesion and proliferation, where it can bind to heparin and calcium. It is formed in, inter alia, muscle and bone tissue.

TSP-4 has a length of 961 amino acids, with amino acids 1 to 26 forming the signal peptide and amino acids 27 to 961 forming the mature protein. For the purposes of illustration, without being restricted thereto, reference is made to the amino acid sequence of thrombospondin-4, which is disclosed herein as SEQ ID NO: 1. The relevant nucleotide and amino acid sequences are obtainable from the NCBI (National Center for Biotechnology Information; National Library of Medicine, Bethesda, Md. 20894, USA; www.ncbi.nlm.nih.gov) under access number UniProtKB-P35443.2 (SEQ ID NO: 1).

```
                                                          (SEQ ID NO: 1)
 1 MLAPRGAAVL LLHLVLQRWL AAGAQATPQV FDLLPSSSQR LNPGALLPVL TDPALNDLYV

61 ISTFKLQTKS SATIFGLYSS TDNSKYFEFT VMGRLNKAIL RYLKNDGKVH LVVFNNLQLA
```

```
121 DGRRHRILLR LSNLQRGAGS LELYLDCIQV DSVHNLPRAF AGPSQKPETI ELRTFQRKPQ

181 DFLEELKLVV RGSLFQVASL QDCFLQQSEP LAATGTGDFN RQFLGQMTQL NQLLGEVKDL

241 LRQQVKETSF LRNTIAECQA CGPLKFQSPT PSTVVPPAPP APPTRPPRRC DSNPCFRGVQ

301 CTDSRDGFQC GPCPEGYTGN GITCIDVDEC KYHPCYPGVH CINLSPGFRC DACPVGFTGP

361 MVQGVGISFA KSNKQVCTDI DECRNGACVP NSICVNTLGS YRCGPCKPGY TGDQIRGCKA

421 ERNCRNPELN PCSVNAQCIE ERQGDVTCVC GVGWAGDGYI CGKDVDIDSY PDEELPCSAR

481 NCKKDNCKYV PNSGQEDADR DGIGDACDED ADGDGILNEQ DNCVLIHNVD QRNSDKDIFG

541 DACDNCLSVL NNDQKDTDGD GRGDACDDDM DGDGIKNILD NCPKFPNRDQ RDKDGDGVGD

601 ACDSCPDVSN PNQSDVDNDL VGDSCDTNQD SDGDGHQDST DNCPTVINSA QLDTDKDGIG

661 DECDDDDDND GIPDLVPPGP DNCRLVPNPA QEDSNSDGVG DICESDFDQD QVIDRIDVCP

721 ENAEVTLTDF RAYQTVVLDP EGDAQIDPNW VVLNQGMEIV QTMNSDPGLA VGYTAFNGVD

781 FEGTFHVNTQ TDDDYAGFIF GYQDSSSFYV VMWKQTEQTY WQATPFRAVA EPGIQLKAVK

841 SKTGPGEHLR NSLWHTGDTS DQVRLLWKDS RNVGWKDKVS YRWFLQHRPQ VGYIRVRFYE

901 GSELVADSGV TIDTTMRGGR LGVFCFSQEN IIWSNLKYRC NDTIPEDFQE FQTQNFDRFD

961 N
```

Another protein of the thrombospondin protein family is cartilage oligomeric matrix protein (COMP), also known as thrombospondin-5. It is an extracellular matrix (ECM) protein which mainly occurs in cartilage. Specifically, COMP occurs in the extracellular matrix which surrounds cells which make up ligaments and tendons, and near cartilage-forming cells (chondrocytes). In humans, the COMP protein is encoded by the COMP gene. Binding to other ECM proteins such as collagen appears to depend on divalent cations. COMP is a marker for cartilage turnover. It appears to have a role in vascular wall remodeling. Furthermore, it appears to play a role in cell growth and cell division and in apoptosis and also in the regulation of cell movement and cell adhesion. It can mediate the interaction of chondrocytes with extracellular cartilage matrix by interaction with cell-surface integrin receptors. The protein consists of five identical glycoprotein subunits, each having EGF-like and calcium-binding (thrombospondin-like) domains which bind strongly to calcium (1, 2, 3, 4, 5, 6, 7, 8, 9).

COMP has a length of 757 amino acids. For the purposes of illustration, without being restricted thereto, reference is made to the amino acid sequence of COMP, which is disclosed herein as SEQ ID NO: 2. The relevant nucleotide and amino acid sequences are obtainable from the NCBI (National Center for Biotechnology Information; National Library of Medicine, Bethesda, Md. 20894, USA; www.ncbi.nlm.nih.gov) under access number UniProtKB-P49747.2 (SEQ ID NO: 2).

```
                                                            (SEQ ID NO: 2)
  1 MVPDTACVLL LTLAALGASG QGQSPLGSDL GPQMLRELQE TNAALQDVRE LLRQQVREIT

61 FLKNTVMECD ACGMQQSVRT GLPSVRPLLH CAPGFCFPGV ACIQTESGAR CGPCPAGFTG

121 NGSHCTDVNE CNAHPCFPRV RCINTSPGFR CEACPPGYSG PTHQGVGLAF AKANKQVCTD

181 INECETGQHN CVPNSVCINT RGSFQCGPCQ PGFVGDQASG CQRRAQRFCP DGSPSECHEH

241 ADCVLERDGS RSCVCAVGWA GNGILCGRDT DLDGFPDEKL RCPERQCRKD NCVTVPNSGQ

301 EDVDRDGIGD ACDPDADGDG VPNEKDNCPL VRNPDQRNTD EDKWGDACDN CRSQKNDDQK

361 DTDQDGRGDA CDDDIDGDRI RNQADNCPRV PNSDQKDSDG DGIGDACDNC PQKSNPDQAD

421 VDHDFVGDAC DSDQDQDGDG HQDSRDNCPT VPNSAQEDSD HDGQGDACDD DDDNDGVPDS

481 RDNCRLVPNP GQEDADRDGV GDVCQDDFDA DKVVDKIDVC PENAEVTLTD FRAFQTVVLD

541 PEGDAQIDPN WVVLNQGREI VQTMNSDPGL AVGYTAFNGV DFEGTFHVNT VTDDDYAGFI

601 FGYQDSSSFY VVMWKQMEQT YWQANPFRAV AEPGIQLKAV KSSTGPGEQL RNALWHTGDT

661 ESQVRLLWKD PRNVGWKDKK SYRWFLQHRP QVGYIRVRFY EGPELVADSN VVLDTTMRGG

721 RLGVFCFSQE NIIWANLRYR CNDTIPEDYE THQLRQA
```

C-type lectin domain family 3 member A (CLEC3A) is a cartilage-specific protein which is expressed to an increased extent in arthrotic cartilage. Besides cartilage, it has so far only been detected in breast cancer tissue. CLEC3A consists of three domains: a highly positively charged N-terminal domain, followed by an alpha-helical oligomerization domain and a C-terminal carbohydrate recognition domain (CRD). CLEC3A binds to laminin and fibronectin and is cut by matrilysin (MMP-7) and other matrix proteases (Tsunezumi, 2009). Recently, a relatively rapid activation of plasminogen by tissue plasminogen activator in the presence of CLEC3A has been shown (10, 11, 12, 13).

CLEC3A has a length of 197 amino acids, with amino acids 1 to 22 forming the signal peptide and amino acids 23 to 197 forming the mature protein. For the purposes of illustration, without being restricted thereto, reference is made to the amino acid sequence of CLEC3A, which is disclosed herein as SEQ ID NO: 3. The relevant nucleotide and amino acid sequences are obtainable from the NCBI (National Center for Biotechnology Information; National Library of Medicine, Bethesda, Md. 20894, USA; www.ncbi.nlm.nih.gov) under access number UniProtKB-O75596.1 SEQ ID NO: 3).

humans) mainly in connective tissue, more precisely in the extracellular matrix). Collagen consists of individual, long collagen molecules which form a left-handed helix. Three at a time of said helices are arranged in a right-handed superhelix. The triple helix is stabilized by hydrogen bonds between the individual strands. Collagen type II, which plays a role in the present application for the diagnosis of arthrosis or of the risk of developing arthrosis, mainly occurs in cartilage and acts as a structural protein in hyaline cartilage and in elastic cartilage. Collagen II is obtained by isolation from cartilage according to the method by Vogel and Paulsson (1984) (14). The relevant nucleotide and amino acid sequences are obtainable from the NCBI (National Center for Biotechnology Information; National Library of Medicine, Bethesda, Md. 20894, USA;

```
                                                          (SEQ ID NO: 3)
   1 MAKNGLVICI LVITLLLDQT TSHTSRLKAR KHSKRRVRDK DGDLKTQIEK LWTEVNALKE

61 IQALQTVCLR GTKVHKKCYL ASEGLKHFHE ANEDCISKGG ILVIPRNSDE INALQDYGKR

121 SLPGVNDFWL GINDMVTEGK FVDVNGIAIS FLNWDRAQPN GGKRENCVLF SQSAQGKWSD

181 EACRSSKRYI CEFTIPQ
```

Collagen (precursor: tropocollagen) is a structural protein which only occurs in multicellular animals (including www.ncbi.nlm.nih.gov) under access number UniProtKB-P02458.3 (SEQ ID NO: 4).

```
                                                          (SEQ ID NO: 4)
    1 MIRLGAPQTL VLLTLLVAAV LRCQGQDVQE AGSCVQDGQR YNDKDVWKPE PCRICVCDTG

61 TVLCDDIICE DVKDCLSPEI PFGECCPICP TDLATASGQP GPKGQKGEPG DIKDIVGPKG

121 PPGPQGPAGE QGPRGDRGDK GEKGAPGPRG RDGEPGTPGN PGPPGPPGPP GPPGLGGNFA

181 AQMAGGFDEK AGGAQLGVMQ GPMGPMGPRG PPGPAGAPGP QGFQGNPGEP GEPGVSGPMG

241 PRGPPGPPGK PGDDGEAGKP GKAGERGPPG PQGARGFPGT PGLPGVKGHR GYPGLDGAKG

301 EAGAPGVKGE SGSPGENGSP GPMGPRGLPG ERGRTGPAGA AGARGNDGQP GPAGPPGPVG

361 PAGGPGFPGA PGAKGEAGPT GARGPEGAQG PRGEPGTPGS PGPAGASGNP GTDGIPGAKG

421 SAGAPGIAGA PGFPGPRGPP GPQGATGPLG PKGQTGEPGI AGFKGEQGPK GEPGPAGPQG

481 APGPAGEEGK RGARGEPGGV GPIGPPGERG APGNRGFPGQ DGLAGPKGAP GERGPSGLAG

541 PKGANGDPGR PGEPGLPGAR GLTGRPGDAG PQGKVGPSGA PGEDGRPGPP GPQGARGQPG

601 VMGFPGPKGA NGEPGKAGEK GLPGAPGLRG LPGKDGETGA AGPPGPAGPA GERGEQGAPG

661 PSGFQGLPGP PGPPGEGGKP GDQGVPGEAG APGLVGPRGE RGFPGERGSP GAQGLQGPRG

721 LPGTPGTDGP KGASGPAGPP GAQGPPGLQG MPGERGAAGI AGPKGDRGDV GEKGPEGAPG

781 KDGGRGLTGP IGPPGPAGAN GEKGEVGPPG PAGSAGARGA PGERGETGPP GPAGFAGPPG

841 ADGQPGAKGE QGEAGQKGDA GAPGPQGPSG APGPQGPTGV TGPKGARGAQ GPPGATGFPG

901 AAGRVGPPGS NGNPGPPGPP GPSGKDGPKG ARGDSGPPGR AGEPGLQGPA GPPGEKGEPG

961 DDGPSGAEGP PGPQGLAGQR GIVGLPGQRG ERGFPGLPGP SGEPGKQGAP GASGDRGPPG

1021 PVGPPGLTGP AGEPGREGSP GADGPPGRDG AAGVKGDRGE TGAVGAPGAP GPPGSPGPAG

1081 PTGKQGDRGE AGAQGPMGPS GPAGARGIQG PQGPRGDKGE AGEPGERGLK GHRGFTGLQG

1141 LPGPPGPSGD QGASGPAGPS GPRGPPGPVG PSGKDGANGI PGPIGPPGPR GRSGETGPAG

1201 PPGNPGPPGP PGPPGPGIDM SAFAGLGPRE KGPDPLQYMR ADQAAGGLRQ HDAEVDATLK
```

```
-continued
1261  SLNNQIESIR  SPEGSRKNPA  RTCRDLKLCH  PEWKSGDYWI  DPNQGCTLDA  MKVFCNMETG

1321  ETCVYPNPAN  VPKKNWWSSK  SKEKKHIWFG  ETINGGFHFS  YGDDNLAPNT  ANVQMTFLRL

1381  LSTEGSQNIT  YHCKNSIAYL  DEAAGNLKKA  LLIQGSNDVE  IRAEGNSRFT  YTALKDGCTK

1441  HTGKWGKTVI  EYRSQKTSRL  PIIDIAPMDI  GGPEQEFGVD  IGPVCFL
```

The term "TSP-4", "COMP", "CLEC3A" or "collagen II", as used herein, is any protein which is known as TSP-4, COMP, CLEC3A or collagen II. The term also encompasses a protein which has identical or similar functions to TSP-4, COMP, CLEC3A or collagen II, identified by SEQ ID NO: 1, SEQ ID NO: 2, SEQ ID NO: 3 and SEQ ID NO: 4. In addition, the proteins can also be known under a different name. Alternatively, the term TSP-4, COMP, CLEC3A or collagen II refers to any protein which has an amino acid identity of at least 50%, 60%, 70%, 80%, 85%, 90%, 95%, 96%, 97%, 98%, or 99% in relation to the sequence of SEQ ID NO: 1, SEQ ID NO: 2, SEQ ID NO: 3 and SEQ ID NO: 4. Alternatively, the term TSP-4, COMP, CLEC3A or collagen II refers to any protein which has an amino acid homology of at least 50%, 60%, 70%, 80%, 85%, 90%, 95% or 100% in relation to the sequence of SEQ ID NO: 1, SEQ ID NO: 2, SEQ ID NO: 3 and SEQ ID NO: 4. Functions or properties of TSP-4, COMP, CLEC3A or collagen II are: TSP-4 forms pentamers and binds to heparin. COMP also forms pentamers, binds to collagen II and is clearly involved in the fibrillogenesis of collagen II. Mutations in the COMP gene can cause PSACH (osteochondrodysplasias pseudoachondroplasia) and MED (multiple epiphyseal dysplasia). CLEC3A leads to a relatively rapid activation of plasminogen by tissue plasminogen activator. Collagen II is a structural component of the extracellular cartilage matrix, forms the basic cartilage scaffold and gives the cartilage its tensile strength. The term TSP-4, COMP, CLEC3A or collagen II covers all proteins to which autoantibodies formed in subjects against TSP-4, COMP, CLEC3A or collagen II bind.

The term "TSP-4", "COMP", "CLEC3A" or "collagen II", as used herein, also refers to a fragment of TSP-4, COMP, CLEC3A or collagen II, so long as said fragment has the ability to bind to autoantibodies formed in subjects against TSP-4, COMP, CLEC3A or collagen II. Preferably, such fragments contain epitopes which the autoantibodies are directed against. More preferably, fragments of TSP-4, COMP, CLEC3A or collagen II have a length of at least 5 amino acids, yet more preferably a length of 5 to 100, yet more preferably a length of 5 to 50, yet more preferably a length of 10 to 50, yet more preferably a length of 15 to 50, yet more preferably a length of 15 to 25 or 40 to 50, amino acids.

The percentage of "amino acid identity", as used herein, refers to the percentage of amino acid residues which are identical at corresponding positions in two sequences optimally aligned to one another. It is determined by comparison of two sequences optimally aligned to one another via a comparison window, wherein the fragment of the amino acid sequence in the comparison window can comprise additions or deletions (e.g., gaps or overhangs) in comparison with the reference sequence SEQ ID NO: 1, SEQ ID NO: 2, SEQ ID NO: 3 and SEQ ID NO: 4, which does not contain said additions or deletions, for optimal alignment of the two sequences. The percentage is calculated by determination of the number of positions at which the identical amino acid residue occurs in both sequences in order to obtain the number of identical positions, division of the number of identical positions by the total number of positions in the comparison window and multiplication of the result by 100. Optimal alignment of the sequences for comparison can be carried out by the homology algorithm from Smith and Waterman, 1981, by the homology alignment algorithm from Needleman and Wunsch, 1970, by the similarity method search from Pearson and Lipman, 1988, by the algorithm from Karlin and Altschul, 1990, modified by Karlin and Altschul, 1993, or by computer implementations of these algorithms (GAP, BESTFIT, BLAST, PASTA and TFASTA in the Wisconsin Genetics Software Packet, Genetics Computer Group (GCG), 575 Science Dr., Madison, Wis.). GAP and BESTFIT are preferably used for determining the optimal alignment. Typically, the standard setting values of 5.00 for "gap weight" and 0.30 for "gap weight" length are used.

The term "percent homology", as used herein, refers to the percentage of amino acid residues which are homologous at corresponding positions in two sequences optimally aligned to one another. The "percent homology" between two sequences is established in a manner substantially identical to what was described above in relation to the determination of "percentage of identity", except for the fact that the calculation also takes homologous positions into account and not just identical positions. Two homologous amino acids are either two identical or two homologous amino acids. Homologous amino acid residues have similar chemical/physical properties, for example amino acids belonging to the same group: aromatic (Phe, Trp, Tyr), acidic (Glu, Asp), polar (Gln, Asn), basic (Lys, Arg, His), aliphatic (Ala, Leu, Ile, Val), having a hydroxyl group (Ser, Thr) or having a short side chain (Gly, Ala, Ser, Thr, Met). Substitutions between such homologous amino acids are expected not to change the protein phenotype (conservative substitutions).

The term "arthrosis" refers to a noninflammatory joint disease that is associated with a change of state, in short it refers to joint attrition or joint wear and tear. Chronic damage to the joint cartilage, usually over a relatively long period, is involved, this showing arthrosis to be a degenerative disease. Over time, the disease also leaves traces in the neighboring tissue, the joint capsule, bone and musculature. The expressions arthrosis deformans, osteoarthrosis, degenerative arthropathy or osteoarthritis, which describe the same clinical picture, are also often used. In this connection, the prefix "osteo" indicates that the joint bone is involved in the disease, too. What are considered to be the cause are an excess of load (for instance, increased body weight), congenital or trauma-related causes such as malalignments of the joints or else osseous deformation due to bone diseases such as osteoporosis. In principle, all joints can be affected by arthritic changes. A distinction is made between various types of arthrosis. In the case of primary arthrosis, a biological inferiority of the cartilage tissue of unclear cause is assumed. Secondary arthroses arise as a result of mechanical overload (for instance, in the case of hip joint dysplasia), inflammatory changes (for instance, in the case of arthritides) or metabolic disorders (for instance, in the case of chondrocalcinosis). Arthrosis can also be associated with effusion due to overload (secondary inflammatory reaction) (activated arthrosis). The term "arthrosis" encompasses osteochondrosis.

Arthrosis is classified according to the radiographic finding into the Kellgren-Lawrence scores 1 to 4 or according to the degree of cartilage damage into the Outerbridge classifications I to IV. In arthrosis, an initial cartilage damage leads to bone changes later on. In stage I of the Outerbridge classification, what occur are roughnesses and thinning of the cartilage layer and tangential fissures. In stage II, hyaline cartilage is replaced with granulation tissue and more inferior fibrocartilage. Pseudocysts composed of necrotic cartilage and bone tissue (detritus cysts) are formed. In stage III, ulcerations already occur, and the connective tissue and the chondrocytes proliferate. In stage IV, the bone plate of a joint flattens. To absorb the pressure on the joint however, bone spurs are formed (osteophytes).

TABLE 1

Overview of radiographic changes for determining Kellgren-Lawrence scores. The line applicable in each case determines the grade.

| Grade | Radiographic findings | | |
|---|---|---|---|
| | Subchondral sclerosis | Joint gap narrowing | Osteophyte formation |
| 1 | slight | not present | not present |
| 2 | indication of irregular joint surface | slight | slight |
| 3 | irregular joint surface clearly identifiable | significant | significant |
| 4 | pronounced joint changes up to complete destruction. Visible deformation/ necrotization of the joint partners | | |

Conventionally, arthrosis is diagnosed differently depending on the joint affected (hand, hip, knee). The main criterion is joint pain (weight-bearing pain, pain on initial movement, fatigue pain, constant pain, night pain, end-phase pain, and pain radiation). Further criteria are typical radiographic findings (see Kellgren-Lawrence score), restrictions in movement (e.g., restriction in inner rotation to below 15° in the hip), brief phase of morning stiffness (<30 min for the knee, <60 min for the hip), joint enlargement/change in the absence of further clinical signs of inflammation, crepitations with palpation of the affected joints, relatively old age (>50 years), ESR <40 mm/h, normal CRP (<5 mg/l), negative RF and anti-CCP. The diagnosis of arthrosis must be made when the main criterion and further clinical or serological criteria are met (for details, see: www.hopkinsarthritis.org/physician-corner/education/arthritis-education-diagnostic-guidelines/(15-17)).

"Rheumatoid arthritis" (RA) is the most common inflammatory disease of the joints. It occurs in approx. 1% of the adult population. The start of the disease is often gradual and is associated with pain in the small finger or toe joints, though other joints can also be affected, especially hand, knee, shoulder, foot and hip joints. Typically, the carpal bones, the metacarpophalangeal joints and the proximal interphalangeal joints are preferentially affected. The affected joints swell and are overheated. A reddening of the affected joints can ensue. These symptoms are usually most pronounced in the morning (morning stiffness). In the course of the disease, more and more joints are affected. Usually, the disease proceeds in bouts; one bout typically lasts between a few weeks and months. The complaints subside between the individual bouts.

RA diagnosis is relatively reliable and is done by laboratory diagnostics, clinical diagnostics and imaging methods in accordance with the ACR/EULAR classification criteria (Aletaha et al., 2010)

TABLE 2

Diagnostic scheme according to the ACR/EULAR criteria. The highest point value reached is awarded per column. The column points are added up. Rheumatoid arthritis is established in the event of ≥6 points and established synovitis in a typical joint (provided that there is no other cause of the synovitis for the inflamed joint). RF = rheumatoid factor, anti-CCP Ab = antibody against cyclic citrullinated peptides, CRP = C-reactive protein, ESR = erythrocyte sedimentation rate.

| Points | Swollen/ painful joints | Serology | Inflammatory parameters in the blood | Duration of symptoms* |
|---|---|---|---|---|
| 0 | ≤1 large joint*** | RF + anti-CCP Ab negative | CRP + ESR normal | <6 weeks |
| 1 | 2-10 large joints*** | | CRP or ESR↑ | ≥6 weeks |
| 2 | 1-3 small joints** | RF or anti-CCP Ab increased | | |
| 3 | 4-10 small joints** | RF or anti-CCP Ab greatly increased (>3-fold over reference value) | | |
| 5 | >10 joints & ≥1 small joint** | | | |

*Of the longest affected joint.
**Metacarpophalangeal joints (MCP) and finger proximal interphalangeal joints (PIP) I-V; metatarsophalangeal joints (MTP) II-V, hallux proximal interphalangeal joints and hand joints. Exclusions are: thumb saddle joints, hallux metatarsophalangeal joints (MTP I), finger and toe distal interphalangeal joints (DIP).
***Ankle, knee, hip, elbow and shoulder joint In the case of the imaging methods, radiographic or MRI examinations are used in order to be able to assess bone damage (erosion). Typical radiological findings are subchondral osteoporosis, destruction of the surrounding bone, ankyloses and joint misalignments (buttenhole deformity, swan neck deformity, ulnar deviation). Using soft-tissue and bone scintigraphy, it is possible to depict quite well the distribution pattern of the inflammatory activity of the various joints.

To diagnose arthrosis or the risk of developing arthrosis in a subject according to the method of the present invention, it is necessary to exclude RA in said subject. This is done using methods known in the specialist field. The term "the subject not having rheumatoid arthritis" therefore means that the subject is tested for RA using common methods. If RA is not established using said methods, then the subject does not have RA in the context of the invention and can be presented to the method of the present invention for diagnosing arthrosis or for diagnosing the risk of developing arthrosis. The exclusion of RA can be done before, during or after the detection of autoantibodies associated with arthrosis, but is preferably done before the diagnosis of arthrosis or the risk of developing arthrosis is carried out.

Autoantibodies are antibodies which are generated by a subject in response to a native protein (autoantigen). Generally, individuals do not generate an immune response to native proteins and therefore do not produce antibodies against them. But in rare cases, endogenous native proteins are recognized as antigens, whereupon B cells, which form such autoantibodies, are stimulated and autoantibodies are produced. This can lead to various autoimmune diseases. The low presentation of bone and cartilage tissue to the immune system may be the reason for the formation of autoantibodies against constituents of cartilage or bone or against neoepitopes which newly arise in the proteolytic degradation of said constituents. In the present invention, use is made of the detection of autoantibodies against extracellular matrix proteins, the degradation products thereof or fragments thereof for diagnosing arthrosis or a degenerative disease of the skeletal system.

The term "autoantibody associated with arthrosis", as used herein, refers to autoantibodies in subjects who are suffering from an arthrosis or who will develop an arthrosis, whereas in subjects without arthrosis or who will not develop an arthrosis, such an autoantibody cannot be detected, for example using the methods referred to here, for example an antibody-based assay method, for example an immunoblotting assay. In the context of the present invention, autoantibodies associated with arthrosis are those which are directed against proteins of the extracellular cartilage matrix, proteins of the subchondral extracellular bone matrix, proteins of the joint capsule or proteins of the extracellular muscle and tendon matrix, thus all proteins which can be released in the context of joint degradation/inflammation processes. Preferably, the autoantibodies are directed against cartilage matrix proteins except for collagen II, and more preferably, the autoantibodies are directed against TSP-4, COMP and/or CLEC3A. In an animal experiment, it was demonstrated that autoantibodies against cartilage matrix proteins such as COMP are of pathophysiological significance and can lead to severe chronic arthritis. Thus, the presence of autoantibodies associated with arthrosis or of autoantibodies associated with a degenerative disease of the skeletal system in a subject is an indication of a pathophysiological role of said autoantibodies in the emergence, the exhibition and the progression of arthrosis or of the degenerative disease of the skeletal system.

As used herein, the term "an autoantibody" encompasses one or more autoantibodies. Thus, the term "detection of an autoantibody" encompasses the detection of one (1) specific autoantibody using, for example, one (1) detection agent and the detection of more than one (1) specific autoantibody, such as 2, 3, 4, 5 or more autoantibodies, using, for example, more than one (1) detection agent, such as 2, 3, 4, 5 or more detection agents.

Cartilage matrix proteins are proteins which occur in the cartilage matrix. Cartilage matrix refers to the extracellular matrix (ECM) of the cartilage tissue, which extracellular matrix is situated between the cartilage cells. The cartilage matrix consists of an unstructured ground substance and an organized network of collagen fibers. It can be divided into two regions: the territorial matrix (capsular matrix) and the interterritorial matrix (interterritories, interterritorial zone). It consists of a dense network of collagen fibers and forms, together with the chondrocytes, the chondrons ("territories"). The territorial matrix surrounds the chondrocytes and encloses them as a result. Typical proteins of the cartilage matrix are collagens (collagen I, II and III), proteins of the thrombospondin family and CLEC3A.

The term "degradation product", as used herein, refers to a fragment of a protein, for example TSP-4, COMP or CLEC3A, which emerged naturally in a subject from the full-length protein as a result of degradation processes, for example under the action of proteases. In this connection, TSP-4, COMP and CLEC3A are, like other proteins of the extracellular matrix, subject to degradation by secreted proteases or membrane proteases at the cellular level. A degradation product can comprise an epitope which is already present in the native protein and is therefore recognized by an autoantibody which also recognizes the native protein owing to the epitope. Alternatively, a degradation product can comprise a neoepitope which is newly formed owing to degradation. Such neoepitopes are normally not recognized by autoantibodies against the native full-length proteins, but can stimulate the formation of new autoantibodies.

As used herein, "detection agent" is understood to mean any molecule, any substance or any reagent which specifically binds to or interacts with the autoantibody. Preferably, the detection agent is capable of binding to the antigen-binding region of the autoantibody. Consequently, in a preferred embodiment of the present invention, the detection agent is the full-length autoantigen, against which the autoantibody is directed, or a fragment thereof. For example, the detection agent is the cartilage matrix protein (autoantigen) itself, against which the autoantibody is directed. For instance, the autoantibody against TSP-4 can be detected by using full-length TSP-4, that against COMP by using full-length COMP or that against CLEC3A by using full-length CLEC3A. The detection agent can also be a fragment of the full-length autoantigen, provided that the fragment is bound by the autoantibody (antigenic fragment). Such a fragment can consist of at least 5, at least 6, at least 7, at least 8, at least 9, at least 10, at least 15, at least 20, at least 25, at least 30, at least 35, at least 40, at least 45, at least 50 or more than 50 amino acid residues of the full-length autoantigen. Such a fragment can also be a degradation product, as defined above. Such a degradation product can comprise a neoepitope which is newly formed as a result of degradation and is not present in the native protein. For the detection of anti-collagen II autoantibodies, the present invention encompasses a detection agent, as defined above, which is specifically directed against anti-collagen II autoantibodies. Said detection agent can be a full-length collagen II protein or a fragment thereof, including a degradation product. Alternatively, a further detection agent is a protein or peptide having an epitope which has an amino acid identity or amino acid homology of at least 50% 60% 70% 80% 85% 90% 95% or 100% in relation to an epitope of a full-length autoantigen, provided that said epitope of the protein or peptide specifically binds to an autoantibody to which the full-length autoantigen (e.g., SEQ ID NO: 1, 2, 3 or 4) binds.

The autoantigen or an antigenic fragment thereof can be produced by methods known to a person skilled in the art. For example, recombinant DNA techniques can be used, it being possible to insert a DNA molecule encoding the autoantigen or a fragment thereof into a suitable expression vector by means of gene technology. It may also be advantageous to construct fusion proteins which facilitate the labeling, immobilization or detection of the antigen (cf. A Laboratory Manual (4th edition), Cold Spring Harbor Laboratory Press, 2012). Alternatively, the autoantigen or an antigenic fragment thereof can be purified from natural sources, for example using protein separation techniques that are well known in the prior art. Such purification techniques encompass, but are not restricted to, molecular-sieve chromatography and/or ion-exchange chromatography. Antigenic fragments of the autoantigen can be identified by methods known in the prior art. For example, degradation products which are recognized by autoantibodies can be identified by immunoblots, purified and sequenced. Since cartilage matrix proteins are known in the prior art, said proteins are also commercially available. For example, TSP-4 and COMP can be purchased from R & D Systems, CLEC3A DNA from Sino Biological and collagen II from Merck.

The detection of an autoantibody in a sample collected from a subject can be achieved by a multiplicity of ways, as known to a person skilled in the art. Exemplary methods encompass, but are not restricted to, antibody-based (immunoassay-based) assay methods, including western blotting methods, immunoblotting methods, enzyme-linked immunsorbent assay (ELISA), sandwich immunoassay, radioimmunoassay (RIA), immunoprecipitation- and dissociation-enhanced lanthanide fluorescence immunoassay (DELFIA), precipitin reaction, gel-diffusion precipitin reaction, immunodiffusion assay, immunoradiometric assay, protein A immunoassay, proteomics methods, surface plasmon resonance (SPR), chemiluminescence, fluorescence polarization, phosphorescence, immunohistochemistry, immunofluorescence, microcytometry, microscopy, fluorescence-activated cell sorting (FACS), flow cytometry, protein microarrays, mass spectrometry-based techniques (including liquid chromatography coupled to tandem mass spectrometry (LC-MS/MS), nano-LC-MS/MS, matrix-assisted laser desorption/ionization mass spectrometry (MALDI-MS), matrix-assisted laser desorption/ionization time-of-flight (MALDI-TOF) mass spectrometry, surface-enhanced laser desorption/ionization mass spectrometry (SELDI-MS), surface-enhanced laser desorption/ionization time-of-flight (SELDI-TOF) mass spectrometry, surface-enhanced affinity capture (SEAC), surface-enhanced neat desorption (SEND) or surface-enhanced photolabile attachment and release (SEPAR) mass spectrometry.

Preferably, the detection is carried out with the aid of a detection agent. This involves contacting a sample from a subject with the antigen under conditions which allow an immunospecific antigen-antibody binding reaction. The antigen can be in solution or can be immobilized on a support. Conversely, the autoantibody can be immobilized on a support. If autoantibodies are present in the sample from the subject, binding to the antigen takes place. In this connection, the preferred detection method is an antibody-based assay method, especially an immunoblotting method, in which, for example, the matrix protein is resolved in a gel, transferred to a membrane the sample from the subject is added and detection is done using a labeled anti-IgG antibody. Further preferred detection methods are immunoassays, slot/dot blot methods, line blot methods, fluorescence detection on cells or tissue, surface plasmon resonance methods or biochip/protein array methods.

"Specifically binds" or "specifically interacts" or "immunospecific" is understood herein to mean that the detection agent essentially only binds to or interacts with the autoantibody which is to be detected, whereas it does not bind to or interact with other substances or only does this to a small degree. "Essentially" or "small degree" means that the detection agent binds to the other substance to an extent of less than 10% 5% 4% 3% 2% or 1% of the degree with which the detection agent specifically binds to the autoantibody.

The detection can be done qualitatively and/or quantitatively. This may require the use of a reference in order to determine whether and/or in what concentration the autoantibody is present in a defined sample amount. Such a reference can be the autoantibody of known concentration, which is, for example, present in a dilution series. To be able to measure the concentration of the autoantibody in a sample from a subject, the detection of the autoantibody in the sample and the dilution series is carried out under identical conditions. Alternatively, such a reference can be the detection reagent, which is, for example, present in a dilution series and binds or interacts with autoantibodies of defined concentration(s), in order to determine the concentration of the autoantibody from the sample of the subject.

The present invention furthermore relates to the method for diagnosing arthrosis or the risk of developing arthrosis of the present invention, wherein the course of arthrosis is monitored, comprising the detection of the autoantibody at various time points; or wherein the stage of arthrosis is diagnosed. The course is characterized by the differing progression of the disease (chronic progressive), for example depending on the reduction of the risk factors or, possibly in the future, depending on the therapy with the drugs that modify the disease course. The disease stage can be subdivided into arthrosis grades (Kellgren-Lawrence score) by means of radiography. Typically, in the course of the disease of the arthrosis patient, said patient passes through the Kellgren-Lawrence stages one after another.

During the progression of arthrosis, the degradation of the extracellular cartilage matrix releases cartilage proteins (joint capsule proteins, subchondral bone proteins, muscle proteins and tendon proteins) or fragments thereof into the synovial fluid and the blood circulation and thus presents them to the immune system, which forms autoantibodies depending on the concentration of the proteins or fragments. Consequently, rising concentrations of autoantibodies indicate a progression of arthrosis, whereas decreasing concentrations of autoantibodies indicate a slowed or stopped progression.

In a 2nd aspect, the present invention furthermore relates to a method for diagnosing a degenerative disease of the skeletal system or the risk of developing a degenerative disease of the skeletal system in a subject, comprising the detection of an autoantibody against thrombospondin-4 (TSP-4) or a degradation product or a fragment thereof or the detection of an autoantibody against COMP or a degradation product or a fragment thereof in a sample originating from the subject.

In one embodiment thereof, the present invention relates to said method of the 2nd aspect, wherein the degenerative disease of the skeletal system encompasses rheumatoid arthritis or arthrosis. In one embodiment thereof, the present invention relates to said method of the 2nd aspect, wherein said method comprises the detection of at least two autoantibodies; preferably wherein said method comprises the detection of an autoantibody against thrombospondin-4 (TSP-4) or a degradation product or a fragment thereof and the detection of an autoantibody against COMP or a degradation product or a fragment thereof; or preferably wherein said method comprises the detection of an autoantibody against thrombospondin-4 (TSP-4) or a degradation product or a fragment thereof and the detection of an autoantibody against CLEC3A or a degradation product or a fragment thereof; more preferably wherein said method comprises the detection of an autoantibody against thrombospondin-4 (TSP-4) or a degradation product or a fragment thereof, the detection of an autoantibody against COMP or a degradation product or a fragment thereof and the detection of an autoantibody against CLEC3A or a degradation product or a fragment thereof.

In one embodiment thereof, the present invention relates to said method of the 2nd aspect, wherein the autoantibody is directed against a neoepitope of a degradation product of a matrix protein.

In one embodiment thereof, the present invention relates to said method of the 2nd aspect, wherein the detection is carried out using a detection agent, preferably wherein the detection agent is capable of binding to the antigen-binding region of the autoantibody, more preferably wherein the detection agent is TSP-4 or a degradation product or a fragment thereof, COMP or a degradation product or a fragment thereof and/or CLEC3A or a degradation product or a fragment thereof.

In one embodiment thereof, the present invention relates to said method of the 2nd aspect, wherein the sample is body fluid, preferably blood, serum, blood plasma, synovial fluid or urine, muscle or cartilage tissue, synovial membrane or tendon.

"Degenerative disease" is generally understood to mean the disease associated with a progressive degeneration. Degeneration refers to functional and/or morphological changes to a cell, a tissue, an organ or the entire organism that represent a deterioration in comparison with full physiological capability, for example constitutionally due to regression, decay, degradation or functional loss or because of chronic damaging factors. "Degenerative disease of the skeletal system", as used herein, is understood to mean the degeneration of the spinal column and the joints or their cartilage constituents, preferably RA or arthrosis.

In a 3rd aspect, the invention furthermore relates to a method for diagnosing arthrosis or the risk of developing arthrosis in a subject, comprising the exclusion of the presence of an autoantibody against collagen II or a degradation product or a fragment thereof, preferably wherein the method comprises the detection, i.e., the step of detection, of an autoantibody against collagen II or a degradation product or a fragment thereof, more preferably wherein the method comprises the detection of an autoantibody against collagen II or a degradation product or a fragment thereof using a detection agent for detecting an autoantibody against collagen II or a degradation product or a fragment thereof.

In one embodiment thereof, the present invention relates to said method of the 3rd aspect, wherein the arthrosis is additionally diagnosed by conventional methods.

In one embodiment thereof, the invention relates to the preceding method of the 3rd aspect for diagnosing arthrosis or the risk of developing arthrosis in a subject, comprising the exclusion of the presence of an autoantibody against collagen II or a degradation product or a fragment thereof, where the subject is diagnosed as having arthrosis in the event of lack of detection of an autoantibody against collagen II or a degradation product or a fragment thereof, whereas the subject is diagnosed as not having arthrosis in the event of detection of an autoantibody against collagen II or a degradation product or a fragment thereof.

The preceding method, comprising the detection of an autoantibody against collagen II or a degradation product or a fragment thereof, can be used alone according to the present invention in order to detect the presence of arthrosis or the nonpresence of arthrosis in a subject. Alternatively, said method can be used in addition to conventional arthrosis diagnosis methods or in addition to the method for diagnosing arthrosis or the risk of developing arthrosis of the present invention with detection of an autoantibody associated with arthrosis. In this connection, the nondetection or the detection of an autoantibody against collagen II or a degradation product or a fragment thereof can be judged to be an additional indication that arthrosis (nondetection) or no arthrosis (detection) is present in the subject.

In one embodiment thereof, the present invention relates to said method of the 3rd aspect, wherein the sample is body fluid, preferably blood, serum, blood plasma, synovial fluid or urine, muscle or cartilage tissue, synovial membrane or tendon.

The present invention furthermore relates to a kit for diagnosing arthrosis or the risk of developing arthrosis in a subject, the subject not having rheumatoid arthritis, comprising a detection agent for detecting an autoantibody associated with arthrosis, preferably wherein the detection agent comprises a detection agent for detecting an autoantibody against TSP-4 or a degradation product or a fragment thereof or a detection agent for detecting an autoantibody against COMP or a degradation product or a fragment thereof.

The present invention furthermore relates to a kit for diagnosing a degenerative disease of the skeletal system or the risk of developing a degenerative disease of the skeletal system in a subject, comprising comprises a detection agent for detecting an autoantibody against TSP-4 or a degradation product or a fragment thereof or a detection agent for detecting an autoantibody against COMP or a degradation product or a fragment thereof, preferably wherein the degenerative disease of the skeletal system encompasses rheumatoid arthritis or arthrosis (including osteochondrosis).

In one embodiment thereof, the present invention relates to the kit as described above, wherein the detection agent comprises at least two detection agents for detecting at least two autoantibodies, preferably wherein the detection agent comprises a detection agent for detecting an autoantibody against TSP-4 or a degradation product or a fragment thereof and a detection agent the detection of an autobody against COMP or a degradation product or a fragment thereof; or preferably wherein the detection agent comprises a detection agent for detecting an autoantibody against TSP-4 or a degradation product or a fragment thereof and a detection agent the detection of an autoantibody against CLEC3A or a degradation product or a fragment thereof; more preferably wherein the detection agent comprises a detection agent for detecting an autoantibody against TSP-4 or a degradation product or a fragment thereof, a detection agent for detecting an autoantibody against COMP or a degradation product or a fragment thereof and a detection agent for detecting an autoantibody against CLEC3A or a degradation product or a fragment thereof.

In one embodiment thereof, the present invention relates to the kit, wherein the kit furthermore comprises a detection agent for detecting an autoantibody against collagen II or a degradation product or a fragment thereof.

The present invention furthermore relates to the use of the kit for diagnosing arthrosis or the risk of developing arthrosis in a subject, the subject not having rheumatoid arthritis; or for diagnosing a degenerative disease of the skeletal system or the risk of developing a degenerative disease of the skeletal system in a subject, preferably wherein the degenerative disease of the skeletal system encompasses rheumatoid arthritis or arthrosis (including osteochondrosis).

The kit can furthermore comprise, in relation to the detection agent, a solid support such as a membrane (e.g., PVDF membrane), a chip, a sensor, a microtiter plate, beads, resin, glass, ceramic or metal coated with a synthetic polymer, glass, ceramic, synthetic polymers and biopolymers, for example crosslinked dextran or agarose, nylon, polyethylene or polystyrene. The detection agent can be already immobilized on the solid support, or support and detection agent are contained in separate containers and the detection agent is applied to the solid support and immobilized thereon before use. The detection agent is preferably present in one or more defined amounts in order to allow the estimation of the amount of the autoantibody in the subject's sample. The kit can furthermore comprise components suitable for carrying out the method of the present invention, for example wash solutions or solutions or devices for carrying out a particular detection method, for example mass spectrometry probes for SELDI such as ProteinChip® arrays or fiber-based sensor devices, etc. A wash solution can be used for washing off sample remnants after application thereof to the solid support to which the detection agent is immobilized, or for washing of remnants of the detection agent applied to a solid support for immobilization. The kit can comprise more than one kind of detection agent against various autoantibodies. For example, the kit can comprise multiple cartilage matrix proteins associated with arthrosis or degradation products or fragments thereof, for example combinations of TSP-4 and COMP, of TSP-4 and CLEC3A or of TSP-4 and COMP and CLEC3A, with or without collagen II, or degradation products or fragments thereof, in separate containers or the same containers.

In a further embodiment, the kit can comprise instructions for carrying out the method of the present invention and/or for interpreting the results, for example in the form of a package insert or a booklet. For example, the instructions can inform the user as to how to obtain the sample, immobilize the detection agent on the solid support if appropriate, wash the support and/or apply the sample. The kit can additionally contain reference detection agent of a defined amount or in multiple defined amounts, the reference detection agent allowing the estimation of the concentration of the autoantibody in the sample. The reference detection agent is, at the same time, the same as the actual detection agent, for example TSP-4, TSP-4 and COMP, TSP-4 and CLEC3A or TSP-4 and COMP and CLEC3A, with or without collagen II, or degradation products or fragments thereof. If the reference is a reference detection agent, the kit can additionally contain autoantibodies of one or more particular concentrations, which may possibly already be immobilized on a solid support, in order to allow comparison with the autoantibody from the sample from the subject. Or the kit can additionally contain reference autoantibodies of a particular amount or in multiple particular amounts, possibly in an additional container or already immobilized on a solid support, the autoantibody allowing the estimation of the concentration of the autoantibody in the sample. The reference autoantibody/antibodies is/are, at the same time, the same as the actual autoantibody/antibodies, for example against TSP-4, TSP-4 and COMP, TSP-4 and CLEC3A or TSP-4 and COMP and CLEC3A, and against or not against collagen II, or degradation products or fragments thereof.

The present invention furthermore relates to an active ingredient for use for treating or preventing an autoimmune-associated arthrosis in a subject, preferably wherein the active ingredient is rituximab. The subject is, in this connection, the subject diagnosed by the present method.

There is currently no drug-based therapy which influences the progression of arthrosis. However, nonsteroidal anti-inflammatory drugs (e.g., ibuprofen, diclofenac, indometacin and naproxen and coxibs) are used to alleviate the complaints, possibly opioids as well in the case of severe pain. In phases of acute joint inflammation, an intra-articular administration of, for example, triamcinolone hexacetonide (glucocorticoid) may be a possibility. The present invention is directed to the detection of autoantibodies associated with arthrosis. In an animal experiment, it was demonstrated that autoantibodies against cartilage matrix proteins such as COMP are of pathophysiological significance and can lead to severe chronic arthritis. Thus, the presence of autoantibodies associated with arthrosis in a subject is an indication of a pathophysiological role of said autoantibodies in the emergence, the exhibition and the progression of arthrosis. The pathophysiology of the autoantibodies therefore allows the application of a specific, individual therapy (personalized therapy) which includes a general immunotherapy for suppressing the formation of autoantibodies and a therapy for suppressing the formation of specific autoantibodies associated with arthrosis. A "targeted therapy" in which a cytostatic is transported to the immune cell by specific binding of an antigen and said immune cell is killed in addition would be conceivable. Consequently, for patients for whom autoantibodies associated with arthrosis are detected, any kind of therapy which reduces the concentration of the autoantibodies, for example by inhibiting the formation of new autoantibodies, is effective. Therefore, one form of therapy in the context of the present invention is immunotherapy or autoimmunotherapy, since it is directed against autoantibodies. Immunotherapies are treatment forms in which the immune system is influenced. In this case, modulating (stimulating and suppressing) or substituting (replacing) methods are used depending on the disease. In the case of autoimmune diseases, suppressing methods which suppress immunological processes, for example the administration of immunosuppressants, are generally used in order to inhibit undesired reactions of the immune system. Common immunosuppressants are, for example, ciclosporin A, tacrolimus, sirolimus, azathioprine and methotrexate. In the context of the present invention, immunosuppressant methods are also used in the treatment of immune-associated arthrosis. Preferably, one therapy used in the context of the present invention is oriented to a reduction in plasma cells or B cells, the therapy preferably being effected by an intra-articular or systemic, particularly preferably intra-articular, administration of an active ingredient which can bring about such a reduction, such as, for example, rituximab, ofatumumab, ocrelizumab and epratuzumab, preferably rituximab. Another form of therapy is a treatment with active ingredients, such as antibodies, which neutralize or inhibit B cell-stimulating cytokines, for example anakinra, infliximab, adalimumab etanercept, tocilizumab. A further form of therapy is the inhibition of the activation and proliferation of B cells by inhibition of signal transduction by, for example, belimumab and atacicept. In this connection, an important role in the activation and proliferation of B cells is attributed to Wnt signal transduction. An effective inhibitor of the Wnt signal transduction cascade is SM04690, of which it was shown in preclinical studies that it has an effect as a "disease-modifying drug" (DMOAD). A further drug which is already authorized is fluoxetine (authorized for treating depressions), which inhibits the Wnt signal transduction cascade and hence also the proliferation of B cells. Consequently, an "active ingredient for use for treating or preventing an autoimmune-associated arthrosis" is an immunosuppressant, an active ingredient for reducing plasma cells or B cells, for example rituximab, an active ingredient, such as an antibody, which neutralizes or inhibits B cell-stimulating cytokines, and/or an active ingredient which inhibits the signal transduction which leads to the activation and proliferation of B cells, for example an active ingredient which inhibits Wnt signal transduction, for example SM04690 or fluoxetine.

In the case of an activated arthrosis, it is not uncommon for the intra-articular administration of cortisone preparations to take place. Cortisone preparations cause a stimulation of the T helper cells, including the TH2 cells, which in turn lead to the activation and proliferation of B cells. Therefore, the administration of cortisone preparations appears to be rather disadvantageous in patients having antibodies associated with arthrosis or having multiple antibodies associated with arthrosis. Subjects who will benefit from an active-ingredient treatment are those for whom antibodies associated with arthrosis are detected using the diagnosis methods of the present invention. The present invention furthermore relates to a method for diagnosing arthrosis or the risk of developing arthrosis or for diagnosing a degenerative disease of the skeletal system or the risk of developing a degenerative disease of the skeletal system in accordance with the present invention, wherein the method is used for therapy selection. If, in the method of diagnosing arthrosis or the risk of developing arthrosis or of diagnosing a degenerative disease of the skeletal system or the risk of developing a degenerative disease of the skeletal system, an antibody associated with arthrosis or the degenerative disease of the skeletal system is detected, the subjects affected can be selected for a therapy in which the arthrosis or the degenerative disease of the skeletal system is treated or prevented by reduction of the concentration of the autoantibodies. Thus, the term "therapy selection" refers to the selection of subjects for whom an arthrosis or degenerative disease of the skeletal system has been diagnosed according to the invention for a therapy in which the concentration of the antibodies is reduced, as described above. In particular, the therapy encompasses an active ingredient for use for treating or preventing an autoimmune-associated arthrosis in a subject, preferably wherein the active ingredient is an antibody against B cells (e.g., rituximab) or a Wnt signaling inhibitor (e.g., fluoxetine or SM04690). The treatment is preferably done intra-articularly.

Further aspects of the invention are:

The present invention is directed to a method for detecting an autoantibody associated with arthrosis or for diagnosing arthrosis or the risk of developing arthrosis in a subject, the subject not having rheumatoid arthritis, wherein the method comprises:
  a) obtaining a sample from the subject; and
  b) detecting whether an autoantibody associated with arthrosis is present in the sample, it being possible for the detection to comprise contacting the sample with a detection agent and detecting the binding between the autoantibody and the detection agent.

The above method can furthermore comprise the steps of:
  i) obtaining a sample from the subject;
  ii) detecting whether an autoantibody against collagen II or a degradation product or fragment thereof is present in the sample, it being possible for the detection to comprise contacting the sample with a detection agent and detecting the binding between the autoantibody and the detection agent.

The present invention is also directed to a method for diagnosing arthrosis or the risk of developing arthrosis in a subject, the subject not having rheumatoid arthritis, wherein the method can comprise:
  a) obtaining a sample from the subject;
  b) detecting whether an autoantibody associated with arthrosis is present in the sample, the detection comprising by contacting the sample with a detection agent and detecting the binding between the autoantibody and the detection agent; and
  c) diagnosing the subject as having arthrosis or a risk of developing arthrosis if an autoantibody associated with arthrosis is detected in the sample.

The above method can furthermore comprise the steps of:
  i) obtaining a sample from the subject;
  ii) detecting whether an autoantibody against collagen II or a degradation product or fragment thereof is present in the sample, it being possible for the detection to comprise contacting the sample with a detection agent and detecting the binding between the autoantibody and the detection agent;
  iii) diagnosing the subject as having arthrosis or a risk of developing arthrosis if an autoantibody against collagen II or a degradation product or fragment thereof is not detected in the sample.

The present invention is also directed to a method for diagnosing arthrosis or the risk of developing arthrosis and treating arthrosis in a subject, the subject not having rheumatoid arthritis, wherein the method comprises:
  a) obtaining a sample from a subject;
  b) detecting whether an autoantibody associated with arthrosis is present in the sample;
  c) diagnosing the subject as having arthrosis or a risk of developing arthrosis if an autoantibody associated with arthrosis is detected in the sample; and
  d) administering an arthrosis treatment to the diagnosed subject.

The above method can furthermore comprise the steps of:
  i) obtaining a sample from the subject;
  ii) detecting whether an autoantibody against collagen II or a degradation product or fragment thereof is present in the sample;
  iii) diagnosing the subject as having arthrosis or a risk of developing arthrosis if an autoantibody against collagen II or a degradation product or fragment thereof is not detected in the sample.

The present invention is also directed to a method for treating or preventing arthrosis in a subject, the subject not having rheumatoid arthritis, wherein the method comprises the administration of an arthrosis treatment to a subject diagnosed in the context of the present invention.

The present invention is also directed to the use of an active ingredient for producing a drug for treating an autoimmune-associated arthrosis in a subject.

The treatment can, in this connection, comprise a treatment in which the concentration of the autoantibodies associated with arthrosis is reduced. For example, the treatment encompasses an immunosuppressant (e.g., ciclosporin A, tacrolimus, sirolimus, azathioprine and methotrexate), an active ingredient for reducing plasma cells or B cells, for example rituximab, ofatumumab, ocrelizumab and epratuzumab, an active ingredient, such as an antibody, which neutralizes or inhibits B cell-stimulating cytokines, for example anakinra, infliximab, adalimumab, etanercept, tocilizumab, and/or an active ingredient which inhibits the signal transduction which leads to the activation and proliferation of B cells, for example an active ingredient which inhibits signal transduction (e.g., belimumab and atacicept) such as, for example, an active ingredient which inhibits Wnt signal transduction, for example SM04690 or fluoxetine.

The present invention is directed to a method for detecting an autoantibody associated with a degenerative disease of the skeletal system or for diagnosing a degenerative disease of the skeletal system or the risk of developing a degenerative disease of the skeletal system in a subject, wherein the method comprises:
  a) obtaining a sample from the subject; and
  b) detecting whether an autoantibody associated with a degenerative disease of the skeletal system is present in the sample, it being possible for the detection to comprise contacting the sample with a detection agent and detecting the binding between the autoantibody and the detection agent.

The present invention is also directed to a method for diagnosing a degenerative disease of the skeletal system or the risk of developing a degenerative disease of the skeletal system in a subject, wherein the method comprises:
 a) obtaining a sample from the subject;
 b) detecting whether an autoantibody associated with a degenerative disease of the skeletal system is present in the sample, it being possible for the detection to comprise contacting the sample with a detection agent and detecting the binding between the autoantibody and the detection agent; and
 c) diagnosing the subject as having a degenerative disease of the skeletal system or a risk of developing a degenerative disease of the skeletal system if an autoantibody associated with a degenerative disease of the skeletal system is detected in the sample.

The present invention is also directed to a method for diagnosing a degenerative disease of the skeletal system or the risk of developing a degenerative disease of the skeletal system and treating a degenerative disease of the skeletal system in a subject, wherein the method comprises:
 a) obtaining a sample from a subject;
 b) detecting whether an autoantibody associated with a degenerative disease of the skeletal system is present in the sample, it being possible for the detection to comprise contacting the sample with a detection agent and detecting the binding between the autoantibody and the detection agent;
 c) diagnosing the subject as having a degenerative disease of the skeletal system or a risk of developing a degenerative disease of the skeletal system if an autoantibody associated with a degenerative disease of the skeletal system is detected in the sample; and
 d) administering a treatment for the degenerative disease of the skeletal system to the diagnosed subject.

The present invention is also directed to a method for treating or preventing a degenerative disease of the skeletal system in a subject, wherein the method comprises the administration of a treatment for the degenerative disease of the skeletal system to a subject diagnosed in the context of the present invention.

The present invention is also directed to the use of an active ingredient for producing a drug for treating a degenerative disease of the skeletal system in a subject.

A drug comprises the active ingredient for treating a disease and a pharmaceutically acceptable carrier that is known in the specialist field. The drug can be formulated for different forms of administration, for example for a local intra-articular or systemic administration (oral, intravenous, subcutaneous, intramuscular). The active ingredient is administered in an effective amount which can be determined by a person skilled in the art or is known to a person skilled in the art, it being possible to orientate the amount of the active ingredient to already known amounts of said active ingredient for treating other diseases. At the same time, the effective amount depends on various factors such as dosage form, age, body weight, sex, duration of treatment and similar factors. The drug can be present as solution, suspension, tablet, capsules or powder, additionally also as paste, ointment, oil, cream, lotion, foam, gel or suppository.

The treatment can, in this connection, comprise a treatment in which the concentration of the autoantibodies associated with the degenerative disease of the skeletal system is reduced. For example, the treatment encompasses an immunosuppressant, an active ingredient for reducing plasma cells or B cells, for example rituximab, an active ingredient, such as an antibody, which neutralizes or inhibits B cell-stimulating cytokines, and/or an active ingredient which inhibits the signal transduction which leads to the activation and proliferation of B cells, for example an active ingredient which inhibits Wnt signal transduction, for example SM04690 or fluoxetine. This kind of treatment is especially effective for the treatment of arthrosis. In the case of RA as well, what takes place according to the invention in the event of detection of an autoantibody against TSP-4 or a degradation product or fragment thereof or against COMP or a degradation product or fragment thereof is the treatment as shown above, thus with an immunosuppressant, an active ingredient for reducing plasma cells or B cells, for example rituximab, an active ingredient, such as an antibody, which neutralizes or inhibits B cell-stimulating cytokines, and/or an active ingredient which inhibits the signal transduction which leads to the activation and proliferation of B cells, for example an active ingredient which inhibits Wnt signal transduction, for example SM04690 or fluoxetine. In this connection, such a treatment, preferably with rituximab, is preferred to be preferred over the treatment of present with, in this order, (1) methotrexate (MTX) as monotherapy or (2) in combination with or as an alternative to the administration of biologicals (preparations completely or virtually identical to endogenous substances) and (3) administration of rituximab in order to avoid joint damage in the initial phase.

The present invention is directed to a method for detecting an autoantibody against collagen II or a degradation product or fragment thereof or for diagnosing arthrosis or the risk of developing arthrosis in a subject, the subject not having rheumatoid arthritis, wherein the method comprises:
 i) obtaining a sample from the subject;
 ii) detecting whether an autoantibody against collagen II or a degradation product or fragment thereof is present in the sample, it being possible for the detection to comprise contacting the sample with a detection agent and detecting the binding between the autoantibody and the detection agent.

The present invention is also directed to a method for diagnosing arthrosis or the risk of developing arthrosis in a subject, the subject not having rheumatoid arthritis, wherein the method comprises:
 i) obtaining a sample from the subject;
 ii) detecting whether an autoantibody against collagen II or a degradation product or fragment thereof is present in the sample, it being possible for the detection to comprise contacting the sample with a detection agent and detecting the binding between the autoantibody and the detection agent;
 iii) diagnosing the subject as having arthrosis or a risk of developing arthrosis if an autoantibody against collagen II or a degradation product or fragment thereof is not detected in the sample.

The present invention is also directed to a method for diagnosing arthrosis or the risk of developing arthrosis and treating arthrosis in a subject, the subject not having rheumatoid arthritis, wherein the method comprises:

i) obtaining a sample from the subject;

ii) detecting whether an autoantibody against collagen II or a degradation product or fragment thereof is present in the sample, it being possible for the detection to comprise contacting the sample with a detection agent and detecting the binding between the autoantibody and the detection agent;

iii) diagnosing the subject as having arthrosis or a risk of developing arthrosis if an autoantibody against collagen II or a degradation product or fragment thereof is not detected in the sample;

iv) administering an arthrosis treatment to the subject.

The treatment is as described above and/or a conventional treatment for alleviating the complaints.

MATERIAL AND METHODS

Selection of Patient and Control Groups

The study population is composed of two patient groups and one healthy control group (HD=healthy donors). The test groups are either arthrosis patients or rheumatoid arthritis (RA) patients. The inclusion criteria for the arthrosis group are a clinically established osteoarthritis (OA) of the large joints. Exclusion criteria are indications of a rheumatoid joint disease or other autoimmune or malignant underlying diseases. Inclusion criteria for the RA group are an established RA in accordance with the ACR/EULAR classification criteria. Exclusion criteria are an arthrosis or other autoimmune or malignant underlying diseases. Inclusion in the control group requires that the subjects be symptom-free in relation to the joints. Exclusion criteria are diagnostic indications of an arthrosis, RA, and autoimmune or malignant underlying diseases. The serum from 10 arthrosis patients, 10 RA patients and 10 healthy controls was tested. All the samples were provided by our cooperation partner Prof. Pongratz of Rheumatologie der Universitätsklinik Düsseldorf [Düsseldorf university hospital, rheumatology].

Cloning, Recombinant Expression and Protein Purification

The human CLEC3A gene was cloned into a modified pCEP-Pu vector and transfected into HEK-293 EBNA cells. The recombinant protein was purified from the supernatant of the cells by affinity chromatography. Human collagen II was purified from human cartilage (PMID: 6439184). Recombinant human TSP-4 (R&D) and recombinant human COMP (R&D) were ordered from the manufacturer in question.

SDS Polyacrylamide Gel Electrophoresis (SDS-PAGE) and Immunoblotting

To detect autoantibodies in the serum from the subjects, the matrix proteins were resolved by means of SDS-PAGE and detected by means of immunoblotting. To this end, the proteins (1 µg in each case per well) were transferred to a PVDF membrane (0.45 µm, Invitrogen) after carrying out the SDS-PAGE (4-12% bis-Tris gels: 12 wells, 1 mm thickness, MOPS buffer, 200 V for 50 min), free binding sites were saturated with 5% milk powder and 1% bovine serum albumin in TBS-T (Tris-buffered saline solution, 0.1% Tween), and were successively incubated with 50 µl of patient serum in 10 ml of blocking solution, overnight at 4° C.) and with an HRP-conjugated (horseradish peroxidase-conjugated) anti-human IgG antibody (SantaCruz, 1:200 000 in blocking solution for 1 h at room temperature). Serum from a healthy person was used as reference. The concentration of IgG in the serum was determined and 0.3, 3 and 30 ng of IgG were loaded onto the SDS-PAGE, each in a reference lane. Signals were detected using the ChemiDoc XRS+ (BioRad) western blot imager after incubation with ECL Plus (Amersham Pharmacia Biotech) and the image sequences were evaluated using ImageLab (BioRad) software.

Results and Discussion

Detection of TSP-4, CLEC3A, COMP and collagen II autoantibodies for the diagnosis of an arthrosis—In our study, we tested the serum from 10 arthrosis (OA) patients, 10 rheumatoid arthritis (RA) patients and 10 healthy subjects (Healthy Donors, HD) for IgG isotype antibodies against TSP-4, CLEC3A, COMP and collagen II by means of SDS-PAGE and immunoblotting (Table 1). The detection of TSP4, CLEC3A, COMP and collagen II autoantibodies in the blood and/or in synovial fluid can be used for the diagnosis, specifically also for an early diagnosis, of an arthrosis or an activated arthrosis and for the diagnosis of the stage of arthrosis, the monitoring of the course of arthrosis and the monitoring of the therapy of an arthrosis (Table 1).

TABLE 1a

Number of positive antibody reactivities against the various matrix proteins in the comparison of OA and HD. Frequencies were each reported in relation to the group size. Significant differences are marked by an *. (source: http://www.socscistatistics.com/tests/fisher/Default2.aspx).

| Antibody against: | OA | HD | Positive prediction value | Negative prediction value | Sensitivity | Specificity | p value |
| --- | --- | --- | --- | --- | --- | --- | --- |
| TSP-4 * | 5/10 | 0/10 | 1 | 0.67 | 0.5 | 1 | 0.0325 |
| COMP | 4/10 | 1/10 | 0.8 | 0.67 | 0.4 | 0.9 | 0.303 |
| CLEC3A | 2/10 | 0/10 | 1 | 0.56 | 0.2 | 1 | 0.474 |
| Collagen II | 0/10 | 7/10 | 0 | 0.23 | 0 | 0.3 | 0.003 |

TABLE 1b

Individual antibody intensities against various antigens. Patients 1 to 10 represent the OA group, patients 11 to 20 the healthy control group. The mean values and standard deviations were calculated for the corresponding group in which there were ≥ two values for the respective antigen. Signals of the immunoblot were evaluated by densitometry and quantified in relation to the associated 0.3 ng IgG reference band (=1) (x-fold IgG) or reported in relation to the group mean value (x-fold MV). If no values were entered in a box, it was not possible to detect a band in the immunoblot. MV = mean value, StdDev = standard deviation.

| | TSP-4 x-fold IgG reference | TSP-4 x-fold MV | COMP x-fold IgG reference | COMP x-fold MV | CLEC3A x-fold IgG reference | CLEC3A x-fold MV | Collagen II x-fold IgG reference | Collagen II x-fold MV |
|---|---|---|---|---|---|---|---|---|
| MV | 0.41 | 1 | 0.27 | 1 | 0.27 | 1 | 0.40 | 1 |
| MV −/+ 2x Std Dev | −0.32 to 1.13 | — | −0.22 to 0.77 | — | 0.12 to 0.42 | — | 0.27 to 0.53 | — |
| Patient 1 | 0.96 | 2.36 | | | | | | |
| Patient 2 | | | 0.15 | 0.55 | 0.19 | 0.72 | | |
| Patient 3 | 0.15 | 0.37 | | | | | | |
| Patient 4 | 0.09 | 0.22 | | | | | | |
| Patient 5 | 0.72 | 1.77 | | | | | | |
| Patient 6 | | | 0.2 | 0.73 | | | | |
| Patient 7 | | | 0.05 | 0.18 | | | | |
| Patient 8 | | | | | | | | |
| Patient 9 | 0.11 | 0.27 | 0.69 | 2.53 | | | | |
| Patient 10 | | | | | 0.34 | 1.28 | | |
| Patient 11 | | | | | | | 0.33 | 0.83 |
| Patient 12 | | | | | | | 0.42 | 1.05 |
| Patient 13 | | | | | | | | |
| Patient 14 | | | | | | | | |
| Patient 15 | | | | | | | 0.53 | 1.33 |
| Patient 16 | | | | | | | 0.35 | 0.88 |
| Patient 17 | | | | | | | 0.34 | 0.85 |
| Patient 18 | | | | | | | 0.39 | 0.98 |
| Patient 19 | | | | | | | 0.44 | 1.10 |
| Patient 20 | | | | | | | | |

By combining the antibodies, it is possible to additionally distinctly increase the diagnostic informative value (Table 2).

TABLE 2

Number of positive antibody reactivities, accumulated, against multiple proteins in groups OA and HD. Frequencies were each reported in relation to the group size. For the cumulative comparisons, the differences in the allocation of the absolute frequencies to the two groups are highly significant. Collagen II autoantibodies could only be detected in the HD group. OA patients showed no collagen II autoantibodies. The lack of detection of collagen II autoantibodies therefore serves as a positive result for OA.

| Antibody group | OA | HD | Positive prediction value | Negative prediction value | Sensitivity | Specificity | P value |
|---|---|---|---|---|---|---|---|
| TSP-4 | 5/10 | 0/10 | 1 | 0.67 | 0.5 | 1 | 0.033 |
| TSP-4/ COMP | 8/10 | 1/10 | 0.89 | 0.82 | 0.8 | 0.9 | 0.005 |
| TSP-4/ COMP/ CLEC3A | 9/10 | 1/10 | 0.9 | 0.9 | 0.9 | 0.9 | 0.001 |
| TSP-4/ COMP/ CLEC3A/ Collagen II | 10/10 | 3/10 | 0.77 | 1.0 | 1.0 | 0.7 | 0.003 |

Detection of TSP-4, CLEC3A and COMP antibodies for therapy selection in the case of arthrosis—In various studies, it has been shown that the immunization of animals with collagen II (CIA, collagen II-induced arthritis) or COMP (COMPIA) leads to a severe, chronic arthritis in the animals. In these (RA) animal models, antibodies against matrix proteins are of pathophysiological significance. This shows that human autoantibodies against matrix proteins can also exhibit a pathophysiological effect and that patients having autoantibodies against matrix proteins are therefore amenable to an immunosuppressant therapy. In this connection, an important criterion for pathogenicity appears to be the number of different autoantibodies and/or the autoantibody concentration (autoantibody titer) in the blood. In our study, there are multiple autoantibodies in two OA patients and the antibody intensities against the different antigens also differ.

Detection of anti-TSP-4 and anti-COMP antibodies in the case of rheumatoid arthritis—In our study population, we found, in three RA patients, concentrations of TSP-4 and COMP autoantibodies (RA patient No. 21, 22, 29) that were higher by a factor of 30-fold to 130-fold compared with the intensities from the other RA patients (Table 3).

TABLE 3

Mean values of the antibody intensities in the RA group. To calculate the mean values, patients 21, 22, 29 were excluded, since they were, statistically speaking, significant outliers (Grubbs' outlier test). MV = mean value, StdDev = standard deviation. Signals of the immunoblot were evaluated by densitometry and quantified in relation to the associated 0.3 ng IgG reference band (=1) (x-fold IgG) or reported in relation to the group mean value (x-fold MV).

|  | TSP-4 x-fold IgG reference | TSP-4 x-fold MV] | COMP x-fold IGg reference | COMP x-fold MV] |
| --- | --- | --- | --- | --- |
| MV | 0.95 | 1 | 0.63 | 1 |
| MV −/+ 2x StdDev | −0.60 to 2.50 | — | −0.05 to 1.32 | — |
| Patient 21 | 1.84 | 1.93 | 82.9 | 130.67 |
| Patient 22 | 30.7 | 32.27 | 0.9 | 1.42 |
| Patient 23 | 1.3 | 1.37 | 0.81 | 1.28 |
| Patient 24 | 0.81 | 0.85 | 1.29 | 2.03 |
| Patient 25 | 0.52 | 0.55 | 0.45 | 0.71 |
| Patient 26 | No band | No band | 0.13 | 0.20 |
| Patient 27 | 0.19 | 0.20 | 0.28 | 0.44 |
| Patient 28 | 0.57 | 0.60 | 0.45 | 0.71 |
| Patient 29 | 51.8 | 54.45 | 0.53 | 0.84 |
| Patient 30 | 2.38 | 2.50 | 0.87 | 1.37 |

REFERENCES

Aletaha D, Neogi T, Silman A J, et al 2010 Rheumatoid arthritis classification criteria: an American College of Rheumatology/European League Against Rheumatism collaborative initiative Annals of the Rheumatic Diseases 2010, 69, 1580-1588
Deane K D., Curr Rheumatol Rep. 2014, 16, 419
Jescke A, et al. Deficiency of thrombospondin-4 in mice does not affect skeletal growth or bone mass acquisition, but causes a transient reduction of articular cartilage thickness. PLOS ONE 2015; DOI 10.1371
Karlin S. and Altschul S. F., PNAS, 1990, 87, 2264-2268
Karlin S. and Altschul S. F., PNAS, 1993, 90, 5873-5877
Lawler J, McHenry K, Duquette M, Derick L (March 1995). "Characterization of human thrombospondin-4". J Biol Chem. 270 (6): 2809-14. doi:10.1074/jbc.270.6.2809. PMID 7852353
Needleman S. B. and Wunsch C. D., J Mol Biol, 1970, 48, 443-453
Orlandi et al., 1989, Proc. Natl. Acad. Sci. USA 86: 3833-3837; and Winter and Milstein, 1991, Nature 349: 293-299
Pearson W. R. and Lipman D. J., PNAS, 1988, 85, 2444-2448
Smith T. F. and Waterman M. S., Add APL Math, 1981, 2, 482-489
Stoll M L, Li Q Z, Zhou J, Punaro M, Olsen N J. Elevated IgG autoantibody production in oligoarticular juvenile idiopathic arthritis may predict a refractory course. Clin Exp Rheumatol. 2011; 29: 736-742.
1. Newton, G., et al., Characterization of human and mouse cartilage oligomeric matrix protein. Genomics, 1994. 24(3): p. 435-9.
2. DiCesare, P. E., et al., Cartilage oligomeric matrix protein: isolation and characterization from human articular cartilage. J Orthop Res, 1995. 13(3): p. 422-8.
3. Acharya, C., et al., Cartilage oligomeric matrix protein and its binding partners in the cartilage extracellular matrix: interaction, regulation and role in chondrogenesis. Matrix Biol, 2014. 37: p. 102-11.
4. Halasz, K., et al., COMP acts as a catalyst in collagen fibrillogenesis. J Biol Chem, 2007. 282(43): p. 31166-73.
5. Haudenschild, D. R., et al., Enhanced activity of transforming growth factor beta1 (TGF-beta1) bound to cartilage oligomeric matrix protein. J Biol Chem, 2011. 286(50): p. 43250-8.
6. Ishida, K., et al., Cartilage oligomeric matrix protein enhances osteogenesis by directly binding and activating bone morphogenetic protein-2. Bone, 2013. 55(1): p. 23-35.
7. Rosenberg, K., et al., Cartilage oligomeric matrix protein shows high affinity zinc-dependent interaction with triple helical collagen. J Biol Chem, 1998. 273(32): p. 20397-403.
8. Kleerekoper, Q., J. T. Hecht, and J. A. Putkey, Disease-causing mutations in cartilage oligomeric matrix protein cause an unstructured Ca2+ binding domain. J Biol Chem, 2002. 277(12): p. 10581-9.
9. Kvansakul, M., J. C. Adams, and E. Hohenester, Structure of a thrombospondin C-terminal fragment reveals a novel calcium core in the type 3 repeats. EMBO J, 2004. 23(6): p. 1223-33.
10. Lau, D., et al., The cartilage-specific lectin C-type lectin domain family 3 member A (CLEC3A) enhances tissue plasminogen activator-mediated plasminogen activation. J Biol Chem, 2017.
11. Karlsson, C., et al., Genome-wide expression profiling reveals new candidate genes associated with osteoarthritis. Osteoarthritis Cartilage, 2010. 18(4): p. 581-92.
12. Tsunezumi, J., S. Higashi, and K. Miyazaki, Matrilysin (MMP-7) cleaves C-type lectin domain family 3 member A (CLEC3A) on tumor cell surface and modulates its cell adhesion activity. J Cell Biochem, 2009. 106(4): p. 693-702.
13. Neame, P. J., H. Tapp, and D. R. Grimm, The cartilage-derived, C-type lectin (CLECSF1): structure of the gene and chromosomal location. Biochim Biophys Acta, 1999. 1446(3): p. 193-202.
14. Vogel, K. G., M. Paulsson, and D. Heinegard, Specific inhibition of type I and type II collagen fibrillogenesis by the small proteoglycan of tendon. Biochem J, 1984. 223(3): p. 587-97.
15. Altman, R. D. Classification of disease: osteoarthritis. in Seminars in arthritis and rheumatism. 1991. Elsevier.
16. Altman, R., et al., Development of criteria for the classification and reporting of osteoarthritis. Classification of osteoarthritis of the knee. Diagnostic and Therapeutic Criteria Committee of the American Rheumatism Association. Arthritis Rheum, 1986. 29(8): p. 1039-49.
17. Altman, R., et al., The American College of Rheumatology criteria for the classification and reporting of osteoarthritis of the hand. Arthritis Rheum, 1990. 33(11): p. 1601-10.

The invention claimed is:

1. A method of treating arthrosis in a subject, the subject not having rheumatoid arthritis, the method comprising:
   (a) obtaining a sample from the subject, wherein the sample is a serum, blood, or plasma sample, and wherein the subject is a human;
   (b) detecting whether an autoantibody against thrombospondin-4 (TSP-4), a degradation product or a fragment thereof, is present in the sample;
   (c) diagnosing the subject as having arthrosis or a risk of developing arthrosis by detecting the autoantibody against thrombospondin-4 (TSP-4), the degradation product or the fragment thereof, in the sample; and
   (d) administering an immunotherapy to the diagnosed subject of step (c).

2. The method of claim 1, wherein the method comprises the exclusion of rheumatoid arthritis in the subject, wherein the subject is tested for rheumatoid arthritis before detecting autoantibody against TSP-4.

3. The method of claim 1, further comprising the exclusion of the presence of an autoantibody against collagen II or a degradation product or a fragment thereof in the sample.

4. The method of claim 3, further comprising detecting the absence of an autoantibody against collagen II or a degradation product or a fragment thereof in the sample.

5. The method of claim 4, wherein the autoantibody against collagen II or a degradation product or a fragment thereof is detected using a detection agent.

6. The method of claim 1, wherein the method comprises the detection of at least one further autoantibody in the subject's sample.

7. The method of claim 6, wherein the at least one further autoantibody is an autoantibody against cartilage oligomeric matrix protein (COMP) or a degradation product or a fragment thereof.

8. The method of claim 1, wherein the detection is carried out using a detection agent.

9. The method of claim 1, wherein the course of arthrosis is monitored by detecting the autoantibody at various time points; or wherein the stage of arthrosis is diagnosed.

10. The method of claim 8, wherein the detection agent is capable of binding to the antigen-binding region of the autoantibody.

11. The method of claim 6, wherein the at least one further autoantibody is an autoantibody against C-type lectin domain family 3 member A (CLEC3A) or a degradation product or a fragment thereof.

12. The method of claim 6, wherein the at least one further autoantibody is an autoantibody against cartilage oligomeric matrix protein (COMP) or a degradation product or a fragment thereof and an autoantibody against C-type lectin domain family 3 member A (CLEC3A) or a degradation product or a fragment thereof.

13. The method of claim 1, wherein the immunotherapy comprises administering to the subject an antibody against B cells and/or a Wnt signaling inhibitor.

14. The method of claim 1, wherein the immunotherapy comprises administering to the subject rituximab, fluoxetine, and/or SM04690.

* * * * *

SEQUENCE LISTING

<160> NUMBER OF SEQ ID NOS: 4

<210> SEQ ID NO 1
<211> LENGTH: 961
<212> TYPE: PRT
<213> ORGANISM: Homo sapiens

<400> SEQUENCE: 1

```
Met Leu Ala Pro Arg Gly Ala Ala Val Leu Leu His Leu Val Leu
1               5                   10                  15

Gln Arg Trp Leu Ala Ala Gly Ala Gln Ala Thr Pro Gln Val Phe Asp
            20                  25                  30

Leu Leu Pro Ser Ser Ser Gln Arg Leu Asn Pro Gly Ala Leu Leu Pro
            35                  40                  45

Val Leu Thr Asp Pro Ala Leu Asn Asp Leu Tyr Val Ile Ser Thr Phe
50                  55                  60

Lys Leu Gln Thr Lys Ser Ser Ala Thr Ile Phe Gly Leu Tyr Ser Ser
65                  70                  75                  80

Thr Asp Asn Ser Lys Tyr Phe Glu Phe Thr Val Met Gly Arg Leu Asn
                85                  90                  95

Lys Ala Ile Leu Arg Tyr Leu Lys Asn Asp Gly Lys Val His Leu Val
                100                 105                 110

Val Phe Asn Asn Leu Gln Leu Ala Asp Gly Arg His Arg Ile Leu
                115                 120                 125

Leu Arg Leu Ser Asn Leu Gln Arg Gly Ala Gly Ser Leu Glu Leu Tyr
                130                 135                 140

Leu Asp Cys Ile Gln Val Asp Ser Val His Asn Leu Pro Arg Ala Phe
145                 150                 155                 160

Ala Gly Pro Ser Gln Lys Pro Glu Thr Ile Glu Leu Arg Thr Phe Gln
                165                 170                 175

Arg Lys Pro Gln Asp Phe Leu Glu Glu Leu Lys Leu Val Val Arg Gly
                180                 185                 190

Ser Leu Phe Gln Val Ala Ser Leu Gln Asp Cys Phe Leu Gln Gln Ser
                195                 200                 205

Glu Pro Leu Ala Ala Thr Gly Thr Gly Asp Phe Asn Arg Gln Phe Leu
                210                 215                 220

Gly Gln Met Thr Gln Leu Asn Gln Leu Leu Gly Glu Val Lys Asp Leu
225                 230                 235                 240

Leu Arg Gln Gln Val Lys Glu Thr Ser Phe Leu Arg Asn Thr Ile Ala
                245                 250                 255

Glu Cys Gln Ala Cys Gly Pro Leu Lys Phe Gln Ser Pro Thr Pro Ser
                260                 265                 270

Thr Val Val Pro Pro Ala Pro Ala Pro Thr Arg Pro Pro Arg
                275                 280                 285

Arg Cys Asp Ser Asn Pro Cys Phe Arg Gly Val Gln Cys Thr Asp Ser
                290                 295                 300

Arg Asp Gly Phe Gln Cys Gly Pro Cys Pro Glu Gly Tyr Thr Gly Asn
305                 310                 315                 320

Gly Ile Thr Cys Ile Asp Val Asp Glu Cys Lys Tyr His Pro Cys Tyr
                325                 330                 335

Pro Gly Val His Cys Ile Asn Leu Ser Pro Gly Phe Arg Cys Asp Ala
                340                 345                 350

Cys Pro Val Gly Phe Thr Gly Pro Met Val Gln Gly Val Gly Ile Ser
                355                 360                 365
```

```
Phe Ala Lys Ser Asn Lys Gln Val Cys Thr Asp Ile Asp Glu Cys Arg
    370             375                 380
Asn Gly Ala Cys Val Pro Asn Ser Ile Cys Val Asn Thr Leu Gly Ser
385             390                 395                 400
Tyr Arg Cys Gly Pro Cys Lys Pro Gly Tyr Thr Gly Asp Gln Ile Arg
                405                 410                 415
Gly Cys Lys Ala Glu Arg Asn Cys Arg Asn Pro Glu Leu Asn Pro Cys
            420                 425                 430
Ser Val Asn Ala Gln Cys Ile Glu Glu Arg Gln Gly Asp Val Thr Cys
                435                 440                 445
Val Cys Gly Val Gly Trp Ala Gly Asp Gly Tyr Ile Cys Gly Lys Asp
450                 455                 460
Val Asp Ile Asp Ser Tyr Pro Asp Glu Glu Leu Pro Cys Ser Ala Arg
465                 470                 475                 480
Asn Cys Lys Lys Asp Asn Cys Lys Tyr Val Pro Asn Ser Gly Gln Glu
                485                 490                 495
Asp Ala Asp Arg Asp Gly Ile Gly Asp Ala Cys Asp Glu Asp Ala Asp
                500                 505                 510
Gly Asp Gly Ile Leu Asn Glu Gln Asp Asn Cys Val Leu Ile His Asn
                515                 520                 525
Val Asp Gln Arg Asn Ser Asp Lys Asp Ile Phe Gly Asp Ala Cys Asp
530                 535                 540
Asn Cys Leu Ser Val Leu Asn Asn Asp Gln Lys Asp Thr Asp Gly Asp
545                 550                 555                 560
Gly Arg Gly Asp Ala Cys Asp Asp Met Asp Gly Asp Gly Ile Lys
                565                 570                 575
Asn Ile Leu Asp Asn Cys Pro Lys Phe Pro Asn Arg Asp Gln Arg Asp
                580                 585                 590
Lys Asp Gly Asp Gly Val Gly Asp Ala Cys Asp Ser Cys Pro Asp Val
            595                 600                 605
Ser Asn Pro Asn Gln Ser Asp Val Asp Asn Asp Leu Val Gly Asp Ser
            610                 615                 620
Cys Asp Thr Asn Gln Asp Ser Asp Gly Asp Gly His Gln Asp Ser Thr
625                 630                 635                 640
Asp Asn Cys Pro Thr Val Ile Asn Ser Ala Gln Leu Asp Thr Asp Lys
                645                 650                 655
Asp Gly Ile Gly Asp Glu Cys Asp Asp Asp Asp Asn Asp Gly Ile
            660                 665                 670
Pro Asp Leu Val Pro Pro Gly Pro Asp Asn Cys Arg Leu Val Pro Asn
            675                 680                 685
Pro Ala Gln Glu Asp Ser Asn Ser Asp Gly Val Gly Asp Ile Cys Glu
            690                 695                 700
Ser Asp Phe Asp Gln Asp Gln Val Ile Asp Arg Ile Asp Val Cys Pro
705                 710                 715                 720
Glu Asn Ala Glu Val Thr Leu Thr Asp Phe Arg Ala Tyr Gln Thr Val
                725                 730                 735
Val Leu Asp Pro Glu Gly Asp Ala Gln Ile Asp Pro Asn Trp Val Val
                740                 745                 750
Leu Asn Gln Gly Met Glu Ile Val Gln Thr Met Asn Ser Asp Pro Gly
            755                 760                 765
Leu Ala Val Gly Tyr Thr Ala Phe Asn Gly Val Asp Phe Glu Gly Thr
            770                 775                 780
Phe His Val Asn Thr Gln Thr Asp Asp Asp Tyr Ala Gly Phe Ile Phe
```

-continued

```
                785                 790                 795                 800
Gly Tyr Gln Asp Ser Ser Phe Tyr Val Val Met Trp Lys Gln Thr
                    805                 810                 815
Glu Gln Thr Tyr Trp Gln Ala Thr Pro Phe Arg Ala Val Ala Glu Pro
            820                 825                 830
Gly Ile Gln Leu Lys Ala Val Lys Ser Lys Thr Gly Pro Gly Glu His
                835                 840                 845
Leu Arg Asn Ser Leu Trp His Thr Gly Asp Thr Ser Asp Gln Val Arg
            850                 855                 860
Leu Leu Trp Lys Asp Ser Arg Asn Val Gly Trp Lys Asp Lys Val Ser
865                 870                 875                 880
Tyr Arg Trp Phe Leu Gln His Arg Pro Gln Val Gly Tyr Ile Arg Val
                885                 890                 895
Arg Phe Tyr Glu Gly Ser Glu Leu Val Ala Asp Ser Gly Val Thr Ile
                900                 905                 910
Asp Thr Thr Met Arg Gly Gly Arg Leu Gly Val Phe Cys Phe Ser Gln
            915                 920                 925
Glu Asn Ile Ile Trp Ser Asn Leu Lys Tyr Arg Cys Asn Asp Thr Ile
        930                 935                 940
Pro Glu Asp Phe Gln Glu Phe Gln Thr Gln Asn Phe Asp Arg Phe Asp
945                 950                 955                 960
Asn

<210> SEQ ID NO 2
<211> LENGTH: 757
<212> TYPE: PRT
<213> ORGANISM: Homo sapiens

<400> SEQUENCE: 2

Met Val Pro Asp Thr Ala Cys Val Leu Leu Leu Thr Leu Ala Ala Leu
1               5                   10                  15
Gly Ala Ser Gly Gln Gly Gln Ser Pro Leu Gly Ser Asp Leu Gly Pro
            20                  25                  30
Gln Met Leu Arg Glu Leu Gln Glu Thr Asn Ala Ala Leu Gln Asp Val
        35                  40                  45
Arg Glu Leu Leu Arg Gln Gln Val Arg Glu Ile Thr Phe Leu Lys Asn
    50                  55                  60
Thr Val Met Glu Cys Asp Ala Cys Gly Met Gln Gln Ser Val Arg Thr
65                  70                  75                  80
Gly Leu Pro Ser Val Arg Pro Leu Leu His Cys Ala Pro Gly Phe Cys
                85                  90                  95
Phe Pro Gly Val Ala Cys Ile Gln Thr Glu Ser Gly Ala Arg Cys Gly
            100                 105                 110
Pro Cys Pro Ala Gly Phe Thr Gly Asn Gly Ser His Cys Thr Asp Val
        115                 120                 125
Asn Glu Cys Asn Ala His Pro Cys Phe Pro Arg Val Arg Cys Ile Asn
    130                 135                 140
Thr Ser Pro Gly Phe Arg Cys Glu Ala Cys Pro Pro Gly Tyr Ser Gly
145                 150                 155                 160
Pro Thr His Gln Gly Val Gly Leu Ala Phe Ala Lys Ala Asn Lys Gln
                165                 170                 175
Val Cys Thr Asp Ile Asn Glu Cys Glu Thr Gly Gln His Asn Cys Val
            180                 185                 190
Pro Asn Ser Val Cys Ile Asn Thr Arg Gly Ser Phe Gln Cys Gly Pro
```

-continued

```
            195                 200                 205
Cys Gln Pro Gly Phe Val Gly Asp Gln Ala Ser Gly Cys Gln Arg Arg
    210                 215                 220
Ala Gln Arg Phe Cys Pro Asp Gly Ser Pro Ser Glu Cys His Glu His
225                 230                 235                 240
Ala Asp Cys Val Leu Glu Arg Asp Gly Ser Arg Ser Cys Val Cys Ala
                245                 250                 255
Val Gly Trp Ala Gly Asn Gly Ile Leu Cys Gly Arg Asp Thr Asp Leu
                260                 265                 270
Asp Gly Phe Pro Asp Glu Lys Leu Arg Cys Pro Glu Arg Gln Cys Arg
                275                 280                 285
Lys Asp Asn Cys Val Thr Val Pro Asn Ser Gly Gln Glu Asp Val Asp
    290                 295                 300
Arg Asp Gly Ile Gly Asp Ala Cys Asp Pro Asp Ala Asp Gly Asp Gly
305                 310                 315                 320
Val Pro Asn Glu Lys Asp Asn Cys Pro Leu Val Arg Asn Pro Asp Gln
                325                 330                 335
Arg Asn Thr Asp Glu Asp Lys Trp Gly Asp Ala Cys Asp Asn Cys Arg
                340                 345                 350
Ser Gln Lys Asn Asp Asp Gln Lys Asp Thr Asp Gln Asp Gly Arg Gly
                355                 360                 365
Asp Ala Cys Asp Asp Ile Asp Gly Asp Arg Ile Arg Asn Gln Ala
    370                 375                 380
Asp Asn Cys Pro Arg Val Pro Asn Ser Asp Gln Lys Asp Ser Asp Gly
385                 390                 395                 400
Asp Gly Ile Gly Asp Ala Cys Asp Asn Cys Pro Gln Lys Ser Asn Pro
                405                 410                 415
Asp Gln Ala Asp Val Asp His Asp Phe Val Gly Asp Ala Cys Asp Ser
                420                 425                 430
Asp Gln Asp Gln Asp Gly Asp Gly His Gln Asp Ser Arg Asp Asn Cys
                435                 440                 445
Pro Thr Val Pro Asn Ser Ala Gln Glu Asp Ser Asp His Asp Gly Gln
    450                 455                 460
Gly Asp Ala Cys Asp Asp Asp Asp Asn Asp Gly Val Pro Asp Ser
465                 470                 475                 480
Arg Asp Asn Cys Arg Leu Val Pro Asn Pro Gly Gln Glu Asp Ala Asp
                485                 490                 495
Arg Asp Gly Val Gly Asp Val Cys Gln Asp Asp Phe Asp Ala Asp Lys
                500                 505                 510
Val Val Asp Lys Ile Asp Val Cys Pro Glu Asn Ala Glu Val Thr Leu
                515                 520                 525
Thr Asp Phe Arg Ala Phe Gln Thr Val Val Leu Asp Pro Glu Gly Asp
    530                 535                 540
Ala Gln Ile Asp Pro Asn Trp Val Val Leu Asn Gln Gly Arg Glu Ile
545                 550                 555                 560
Val Gln Thr Met Asn Ser Asp Pro Gly Leu Ala Val Gly Tyr Thr Ala
                565                 570                 575
Phe Asn Gly Val Asp Phe Glu Gly Thr Phe His Val Asn Thr Val Thr
                580                 585                 590
Asp Asp Asp Tyr Ala Gly Phe Ile Phe Gly Tyr Gln Asp Ser Ser Ser
                595                 600                 605
Phe Tyr Val Val Met Trp Lys Gln Met Glu Gln Thr Tyr Trp Gln Ala
    610                 615                 620
```

```
Asn Pro Phe Arg Ala Val Ala Glu Pro Gly Ile Gln Leu Lys Ala Val
625                 630                 635                 640

Lys Ser Ser Thr Gly Pro Gly Glu Gln Leu Arg Asn Ala Leu Trp His
            645                 650                 655

Thr Gly Asp Thr Glu Ser Gln Val Arg Leu Leu Trp Lys Asp Pro Arg
        660                 665                 670

Asn Val Gly Trp Lys Asp Lys Ser Tyr Arg Trp Phe Leu Gln His
        675                 680                 685

Arg Pro Gln Val Gly Tyr Ile Arg Val Arg Phe Tyr Glu Gly Pro Glu
    690                 695                 700

Leu Val Ala Asp Ser Asn Val Val Leu Asp Thr Thr Met Arg Gly Gly
705                 710                 715                 720

Arg Leu Gly Val Phe Cys Phe Ser Gln Glu Asn Ile Ile Trp Ala Asn
                725                 730                 735

Leu Arg Tyr Arg Cys Asn Asp Thr Ile Pro Glu Asp Tyr Glu Thr His
            740                 745                 750

Gln Leu Arg Gln Ala
            755

<210> SEQ ID NO 3
<211> LENGTH: 197
<212> TYPE: PRT
<213> ORGANISM: Homo sapiens

<400> SEQUENCE: 3

Met Ala Lys Asn Gly Leu Val Ile Cys Ile Leu Val Ile Thr Leu Leu
1               5                   10                  15

Leu Asp Gln Thr Thr Ser His Thr Ser Arg Leu Lys Ala Arg Lys His
            20                  25                  30

Ser Lys Arg Arg Val Arg Asp Lys Asp Gly Asp Leu Lys Thr Gln Ile
        35                  40                  45

Glu Lys Leu Trp Thr Glu Val Asn Ala Leu Lys Glu Ile Gln Ala Leu
    50                  55                  60

Gln Thr Val Cys Leu Arg Gly Thr Lys Val His Lys Lys Cys Tyr Leu
65                  70                  75                  80

Ala Ser Glu Gly Leu Lys His Phe His Glu Ala Asn Glu Asp Cys Ile
                85                  90                  95

Ser Lys Gly Gly Ile Leu Val Ile Pro Arg Asn Ser Asp Glu Ile Asn
            100                 105                 110

Ala Leu Gln Asp Tyr Gly Lys Arg Ser Leu Pro Gly Val Asn Asp Phe
        115                 120                 125

Trp Leu Gly Ile Asn Asp Met Val Thr Glu Gly Lys Phe Val Asp Val
    130                 135                 140

Asn Gly Ile Ala Ile Ser Phe Leu Asn Trp Asp Arg Ala Gln Pro Asn
145                 150                 155                 160

Gly Gly Lys Arg Glu Asn Cys Val Leu Phe Ser Gln Ser Ala Gln Gly
                165                 170                 175

Lys Trp Ser Asp Glu Ala Cys Arg Ser Ser Lys Arg Tyr Ile Cys Glu
            180                 185                 190

Phe Thr Ile Pro Gln
            195

<210> SEQ ID NO 4
<211> LENGTH: 1487
<212> TYPE: PRT
```

<213> ORGANISM: Homo sapiens

<400> SEQUENCE: 4

| | | | | | | | | | | | | | | |
|---|---|---|---|---|---|---|---|---|---|---|---|---|---|---|
| Met | Ile | Arg | Leu | Gly | Ala | Pro | Gln | Thr | Leu | Val | Leu | Leu | Thr | Leu | Leu |
| 1 | | | | 5 | | | | | 10 | | | | | 15 | |
| Val | Ala | Ala | Val | Leu | Arg | Cys | Gln | Gly | Gln | Asp | Val | Gln | Glu | Ala | Gly |
| | | | 20 | | | | | 25 | | | | | 30 | | |
| Ser | Cys | Val | Gln | Asp | Gly | Gln | Arg | Tyr | Asn | Asp | Lys | Asp | Val | Trp | Lys |
| | | 35 | | | | | 40 | | | | | 45 | | | |
| Pro | Glu | Pro | Cys | Arg | Ile | Cys | Val | Cys | Asp | Thr | Gly | Thr | Val | Leu | Cys |
| | 50 | | | | | 55 | | | | | 60 | | | | |
| Asp | Asp | Ile | Ile | Cys | Glu | Asp | Val | Lys | Asp | Cys | Leu | Ser | Pro | Glu | Ile |
| 65 | | | | | 70 | | | | | 75 | | | | | 80 |
| Pro | Phe | Gly | Glu | Cys | Cys | Pro | Ile | Cys | Pro | Thr | Asp | Leu | Ala | Thr | Ala |
| | | | | 85 | | | | | 90 | | | | | 95 | |
| Ser | Gly | Gln | Pro | Gly | Pro | Lys | Gly | Gln | Lys | Gly | Glu | Pro | Gly | Asp | Ile |
| | | | 100 | | | | | 105 | | | | | 110 | | |
| Lys | Asp | Ile | Val | Gly | Pro | Lys | Gly | Pro | Pro | Gly | Pro | Gln | Gly | Pro | Ala |
| | | 115 | | | | | 120 | | | | | 125 | | | |
| Gly | Glu | Gln | Gly | Pro | Arg | Gly | Asp | Arg | Gly | Asp | Lys | Gly | Glu | Lys | Gly |
| | 130 | | | | | 135 | | | | | 140 | | | | |
| Ala | Pro | Gly | Pro | Arg | Gly | Arg | Asp | Gly | Glu | Pro | Gly | Thr | Pro | Gly | Asn |
| 145 | | | | | 150 | | | | | 155 | | | | | 160 |
| Pro | Gly | Pro | Pro | Gly | Pro | Pro | Gly | Pro | Pro | Gly | Pro | Pro | Gly | Leu | Gly |
| | | | | 165 | | | | | 170 | | | | | 175 | |
| Gly | Asn | Phe | Ala | Ala | Gln | Met | Ala | Gly | Gly | Phe | Asp | Glu | Lys | Ala | Gly |
| | | | 180 | | | | | 185 | | | | | 190 | | |
| Gly | Ala | Gln | Leu | Gly | Val | Met | Gln | Gly | Pro | Met | Gly | Pro | Met | Gly | Pro |
| | | 195 | | | | | 200 | | | | | 205 | | | |
| Arg | Gly | Pro | Pro | Gly | Pro | Ala | Gly | Ala | Pro | Gly | Pro | Gln | Gly | Phe | Gln |
| | 210 | | | | | 215 | | | | | 220 | | | | |
| Gly | Asn | Pro | Gly | Glu | Pro | Gly | Glu | Pro | Gly | Val | Ser | Gly | Pro | Met | Gly |
| 225 | | | | | 230 | | | | | 235 | | | | | 240 |
| Pro | Arg | Gly | Pro | Pro | Gly | Pro | Pro | Gly | Lys | Pro | Gly | Asp | Asp | Gly | Glu |
| | | | | 245 | | | | | 250 | | | | | 255 | |
| Ala | Gly | Lys | Pro | Gly | Lys | Ala | Gly | Glu | Arg | Gly | Pro | Pro | Gly | Pro | Gln |
| | | | 260 | | | | | 265 | | | | | 270 | | |
| Gly | Ala | Arg | Gly | Phe | Pro | Gly | Thr | Pro | Gly | Leu | Pro | Gly | Val | Lys | Gly |
| | | 275 | | | | | 280 | | | | | 285 | | | |
| His | Arg | Gly | Tyr | Pro | Gly | Leu | Asp | Gly | Ala | Lys | Gly | Glu | Ala | Gly | Ala |
| | 290 | | | | | 295 | | | | | 300 | | | | |
| Pro | Gly | Val | Lys | Gly | Glu | Ser | Gly | Ser | Pro | Gly | Glu | Asn | Gly | Ser | Pro |
| 305 | | | | | 310 | | | | | 315 | | | | | 320 |
| Gly | Pro | Met | Gly | Pro | Arg | Gly | Leu | Pro | Gly | Glu | Arg | Gly | Arg | Thr | Gly |
| | | | | 325 | | | | | 330 | | | | | 335 | |
| Pro | Ala | Gly | Ala | Ala | Gly | Ala | Arg | Gly | Asn | Asp | Gly | Gln | Pro | Gly | Pro |
| | | | 340 | | | | | 345 | | | | | 350 | | |
| Ala | Gly | Pro | Pro | Gly | Pro | Val | Gly | Pro | Ala | Gly | Gly | Pro | Gly | Phe | Pro |
| | | 355 | | | | | 360 | | | | | 365 | | | |
| Gly | Ala | Pro | Gly | Ala | Lys | Gly | Glu | Ala | Gly | Pro | Thr | Gly | Ala | Arg | Gly |
| | 370 | | | | | 375 | | | | | 380 | | | | |
| Pro | Glu | Gly | Ala | Gln | Gly | Pro | Arg | Gly | Glu | Pro | Gly | Thr | Pro | Gly | Ser |
| 385 | | | | | 390 | | | | | 395 | | | | | 400 |

```
Pro Gly Pro Ala Gly Ala Ser Gly Asn Pro Gly Thr Asp Gly Ile Pro
                405                 410                 415

Gly Ala Lys Gly Ser Ala Gly Ala Pro Gly Ile Ala Gly Ala Pro Gly
        420                 425                 430

Phe Pro Gly Pro Arg Gly Pro Pro Gly Pro Gln Gly Ala Thr Gly Pro
            435                 440                 445

Leu Gly Pro Lys Gly Gln Thr Gly Glu Pro Gly Ile Ala Gly Phe Lys
    450                 455                 460

Gly Glu Gln Gly Pro Lys Gly Glu Pro Gly Ala Gly Pro Gln Gly
465                 470                 475                 480

Ala Pro Gly Pro Ala Gly Glu Glu Gly Lys Arg Gly Ala Arg Gly Glu
                485                 490                 495

Pro Gly Gly Val Gly Pro Ile Gly Pro Pro Gly Glu Arg Gly Ala Pro
                500                 505                 510

Gly Asn Arg Gly Phe Pro Gly Gln Asp Gly Leu Ala Gly Pro Lys Gly
            515                 520                 525

Ala Pro Gly Glu Arg Gly Pro Ser Gly Leu Ala Gly Pro Lys Gly Ala
    530                 535                 540

Asn Gly Asp Pro Gly Arg Pro Gly Glu Pro Gly Leu Pro Gly Ala Arg
545                 550                 555                 560

Gly Leu Thr Gly Arg Pro Gly Asp Ala Gly Pro Gln Gly Lys Val Gly
                565                 570                 575

Pro Ser Gly Ala Pro Gly Glu Asp Gly Arg Pro Gly Pro Pro Gly Pro
            580                 585                 590

Gln Gly Ala Arg Gly Gln Pro Gly Val Met Gly Phe Pro Gly Pro Lys
            595                 600                 605

Gly Ala Asn Gly Glu Pro Gly Lys Ala Gly Glu Lys Gly Leu Pro Gly
    610                 615                 620

Ala Pro Gly Leu Arg Gly Leu Pro Gly Lys Asp Gly Glu Thr Gly Ala
625                 630                 635                 640

Ala Gly Pro Pro Gly Pro Ala Gly Pro Ala Gly Glu Arg Gly Glu Gln
                645                 650                 655

Gly Ala Pro Gly Pro Ser Gly Phe Gln Gly Leu Pro Gly Pro Pro Gly
            660                 665                 670

Pro Pro Gly Glu Gly Gly Lys Pro Gly Asp Gln Gly Val Pro Gly Glu
            675                 680                 685

Ala Gly Ala Pro Gly Leu Val Gly Pro Arg Gly Glu Arg Gly Phe Pro
    690                 695                 700

Gly Glu Arg Gly Ser Pro Gly Ala Gln Gly Leu Gln Gly Pro Arg Gly
705                 710                 715                 720

Leu Pro Gly Thr Pro Gly Thr Asp Gly Pro Lys Gly Ala Ser Gly Pro
                725                 730                 735

Ala Gly Pro Pro Gly Ala Gln Gly Pro Pro Gly Leu Gln Gly Met Pro
            740                 745                 750

Gly Glu Arg Gly Ala Ala Gly Ile Ala Gly Pro Lys Gly Asp Arg Gly
            755                 760                 765

Asp Val Gly Glu Lys Gly Pro Glu Gly Ala Pro Gly Lys Asp Gly Gly
    770                 775                 780

Arg Gly Leu Thr Gly Pro Ile Gly Pro Pro Gly Pro Ala Gly Ala Asn
785                 790                 795                 800

Gly Glu Lys Gly Glu Val Gly Pro Pro Gly Pro Ala Gly Ser Ala Gly
                805                 810                 815

Ala Arg Gly Ala Pro Gly Glu Arg Gly Glu Thr Gly Pro Pro Gly Pro
```

```
                820                 825                 830
Ala Gly Phe Ala Gly Pro Pro Gly Ala Asp Gly Gln Pro Gly Ala Lys
            835                 840                 845
Gly Glu Gln Gly Glu Ala Gly Gln Lys Gly Asp Ala Gly Ala Pro Gly
850                 855                 860
Pro Gln Gly Pro Ser Gly Ala Pro Gly Pro Gln Gly Pro Thr Gly Val
865                 870                 875                 880
Thr Gly Pro Lys Gly Ala Arg Gly Ala Gln Gly Pro Pro Gly Ala Thr
                885                 890                 895
Gly Phe Pro Gly Ala Ala Gly Arg Val Gly Pro Pro Gly Ser Asn Gly
            900                 905                 910
Asn Pro Gly Pro Pro Gly Pro Pro Gly Pro Ser Gly Lys Asp Gly Pro
        915                 920                 925
Lys Gly Ala Arg Gly Asp Ser Gly Pro Pro Gly Arg Ala Gly Glu Pro
    930                 935                 940
Gly Leu Gln Gly Pro Ala Gly Pro Pro Gly Glu Lys Gly Glu Pro Gly
945                 950                 955                 960
Asp Asp Gly Pro Ser Gly Ala Glu Gly Pro Pro Gly Pro Gln Gly Leu
                965                 970                 975
Ala Gly Gln Arg Gly Ile Val Gly Leu Pro Gly Gln Arg Gly Glu Arg
            980                 985                 990
Gly Phe Pro Gly Leu Pro Gly Pro Ser Gly Glu Pro Gly Lys Gln Gly
        995                 1000                1005
Ala Pro Gly Ala Ser Gly Asp Arg Gly Pro Pro Gly Pro Val Gly
    1010                1015                1020
Pro Pro Gly Leu Thr Gly Pro Ala Gly Glu Pro Gly Arg Glu Gly
    1025                1030                1035
Ser Pro Gly Ala Asp Gly Pro Pro Gly Arg Asp Gly Ala Ala Gly
    1040                1045                1050
Val Lys Gly Asp Arg Gly Glu Thr Gly Ala Val Gly Ala Pro Gly
    1055                1060                1065
Ala Pro Gly Pro Pro Gly Ser Pro Gly Pro Ala Gly Pro Thr Gly
    1070                1075                1080
Lys Gln Gly Asp Arg Gly Glu Ala Gly Ala Gln Gly Pro Met Gly
    1085                1090                1095
Pro Ser Gly Pro Ala Gly Ala Arg Gly Ile Gln Gly Pro Gln Gly
    1100                1105                1110
Pro Arg Gly Asp Lys Gly Glu Ala Gly Glu Pro Gly Glu Arg Gly
    1115                1120                1125
Leu Lys Gly His Arg Gly Phe Thr Gly Leu Gln Gly Leu Pro Gly
    1130                1135                1140
Pro Pro Gly Pro Ser Gly Asp Gln Gly Ala Ser Gly Pro Ala Gly
    1145                1150                1155
Pro Ser Gly Pro Arg Gly Pro Pro Gly Pro Val Gly Pro Ser Gly
    1160                1165                1170
Lys Asp Gly Ala Asn Gly Ile Pro Gly Pro Ile Gly Pro Pro Gly
    1175                1180                1185
Pro Arg Gly Arg Ser Gly Glu Thr Gly Pro Ala Gly Pro Pro Gly
    1190                1195                1200
Asn Pro Gly Pro Pro Gly Pro Pro Gly Pro Pro Gly Pro Gly Ile
    1205                1210                1215
Asp Met Ser Ala Phe Ala Gly Leu Gly Pro Arg Glu Lys Gly Pro
    1220                1225                1230
```

-continued

```
Asp Pro Leu Gln Tyr Met Arg Ala Asp Gln Ala Ala Gly Gly Leu
    1235                1240            1245

Arg Gln His Asp Ala Glu Val Asp Ala Thr Leu Lys Ser Leu Asn
    1250            1255            1260

Asn Gln Ile Glu Ser Ile Arg Ser Pro Glu Gly Ser Arg Lys Asn
    1265            1270            1275

Pro Ala Arg Thr Cys Arg Asp Leu Lys Leu Cys His Pro Glu Trp
    1280            1285            1290

Lys Ser Gly Asp Tyr Trp Ile Asp Pro Asn Gln Gly Cys Thr Leu
    1295            1300            1305

Asp Ala Met Lys Val Phe Cys Asn Met Glu Thr Gly Glu Thr Cys
    1310            1315            1320

Val Tyr Pro Asn Pro Ala Asn Val Pro Lys Lys Asn Trp Trp Ser
    1325            1330            1335

Ser Lys Ser Lys Glu Lys Lys His Ile Trp Phe Gly Glu Thr Ile
    1340            1345            1350

Asn Gly Gly Phe His Phe Ser Tyr Gly Asp Asp Asn Leu Ala Pro
    1355            1360            1365

Asn Thr Ala Asn Val Gln Met Thr Phe Leu Arg Leu Leu Ser Thr
    1370            1375            1380

Glu Gly Ser Gln Asn Ile Thr Tyr His Cys Lys Asn Ser Ile Ala
    1385            1390            1395

Tyr Leu Asp Glu Ala Ala Gly Asn Leu Lys Lys Ala Leu Leu Ile
    1400            1405            1410

Gln Gly Ser Asn Asp Val Glu Ile Arg Ala Glu Gly Asn Ser Arg
    1415            1420            1425

Phe Thr Tyr Thr Ala Leu Lys Asp Gly Cys Thr Lys His Thr Gly
    1430            1435            1440

Lys Trp Gly Lys Thr Val Ile Glu Tyr Arg Ser Gln Lys Thr Ser
    1445            1450            1455

Arg Leu Pro Ile Ile Asp Ile Ala Pro Met Asp Ile Gly Gly Pro
    1460            1465            1470

Glu Gln Glu Phe Gly Val Asp Ile Gly Pro Val Cys Phe Leu
    1475            1480            1485
```